United States Patent
Takeda et al.

(10) Patent No.: US 11,583,221 B2
(45) Date of Patent: Feb. 21, 2023

(54) COGNITIVE IMPAIRMENT DIAGNOSTIC APPARATUS AND COGNITIVE IMPAIRMENT DIAGNOSTIC PROGRAM

(71) Applicant: OSAKA UNIVERSITY, Osaka (JP)

(72) Inventors: Shuko Takeda, Osaka (JP); Ryuichi Morishita, Osaka (JP); Akane Oyama, Osaka (JP); Tsuneo Nakajima, Osaka (JP)

(73) Assignee: OSAKA UNIVERSITY, Osaka (JP)

( * ) Notice: Subject to any disclaimer, the term of this patent is extended or adjusted under 35 U.S.C. 154(b) by 401 days.

(21) Appl. No.: 16/763,829

(22) PCT Filed: Nov. 13, 2018

(86) PCT No.: PCT/JP2018/041932
§ 371 (c)(1),
(2) Date: May 13, 2020

(87) PCT Pub. No.: WO2019/098173
PCT Pub. Date: May 23, 2019

(65) Prior Publication Data
US 2020/0383626 A1    Dec. 10, 2020

(30) Foreign Application Priority Data

Nov. 14, 2017    (JP) .............................. JP2017-219321

(51) Int. Cl.
*A61B 5/00* (2006.01)
*A61B 5/16* (2006.01)

(52) U.S. Cl.
CPC ............ *A61B 5/4088* (2013.01); *A61B 5/163* (2017.08); *A61B 5/743* (2013.01)

(58) Field of Classification Search
CPC ....... A61B 5/4088; A61B 5/163; A61B 5/743; A61B 3/113; A61B 10/00; G16H 50/20
(Continued)

(56) References Cited

U.S. PATENT DOCUMENTS

| 5,305,764 A | 4/1994 | Yamada et al. |
| 5,311,879 A | 5/1994 | Yamada et al. |

(Continued)

FOREIGN PATENT DOCUMENTS

| EP | 0582772 | 2/1994 |
| JP | 6-70884 | 3/1994 |

(Continued)

OTHER PUBLICATIONS

International Search Report (ISR) dated Jan. 15, 2019 in International (PCT) Application No. PCT/JP2018/041932.

(Continued)

*Primary Examiner* — Mohammed A Hasan
(74) *Attorney, Agent, or Firm* — Wenderoth, Lind & Ponack, L.L.P.

(57) ABSTRACT

A cognitive impairment diagnostic apparatus includes: a display which displays a video for diagnosis of cognitive impairment on a display surface; an imaging unit which captures images of an eye of a subject; a detection unit which detects viewpoints of the subject on the display surface in time series based on the images captured by the imaging unit; a creation unit which creates a distribution map representing a distribution of the viewpoints detected by the detection unit; a storage unit which stores case characteristic data indicating a characteristic of a viewpoint distribution corresponding to a typical case in cognitive impairment; and a diagnostic unit which diagnoses cognitive impairment of the subject by determining whether the distribution map has the characteristic indicated by the case characteristic data.

11 Claims, 23 Drawing Sheets

(58) Field of Classification Search
USPC .......................................................... 600/558
See application file for complete search history.

(56) References Cited

U.S. PATENT DOCUMENTS

| | | |
|---|---|---|
| 2004/0207813 A1 | 10/2004 | Suzuki |
| 2011/0116041 A1 | 5/2011 | Hartung et al. |
| 2014/0213930 A1 | 7/2014 | Mori et al. |
| 2015/0050628 A1 | 2/2015 | Mori et al. |
| 2016/0106358 A1 | 4/2016 | Macknik et al. |
| 2016/0279238 A1 | 9/2016 | Neumann et al. |
| 2017/0367606 A1* | 12/2017 | Lee .................... A61H 1/001 |
| 2019/0221313 A1* | 7/2019 | Rim .................... A61B 3/1176 |

FOREIGN PATENT DOCUMENTS

| | | |
|---|---|---|
| JP | 6-70885 | 3/1994 |
| JP | 2004-49564 | 2/2004 |
| JP | 2007-130495 | 5/2007 |
| JP | 4116354 | 7/2008 |
| JP | 4560801 | 10/2010 |
| JP | 2011-515189 | 5/2011 |
| JP | 2013-52116 | 3/2013 |
| JP | 2013-150668 | 8/2013 |
| JP | 2013-150669 | 8/2013 |
| JP | 2013-169375 | 9/2013 |
| JP | 2013-223713 | 10/2013 |
| JP | 5761048 | 8/2015 |
| JP | 5761049 | 8/2015 |
| JP | 5817582 | 11/2015 |
| JP | 5912351 | 4/2016 |
| JP | 5926210 | 5/2016 |
| JP | 2016-523112 | 8/2016 |
| JP | 2017-501848 | 1/2017 |
| JP | 2017-140335 | 8/2017 |
| JP | 2017-158866 | 9/2017 |
| JP | 2017-176302 | 10/2017 |
| WO | 2010/045356 | 4/2010 |
| WO | 2014/193564 | 12/2014 |

OTHER PUBLICATIONS

Extended European Search Report dated Jul. 16, 2021 in corresponding European Patent Application No. 18878289.0.
Lagun et al., "Detecting cognitive impairment by eye movement analysis using automatic classification algorithms", Journal of Neuroscience Methods, Jun. 2011, vol. 201, pp. 196-203.
Crawford et al., "Inhibitory Control of Saccadic Eye Movements and Cognitive Impairment in Alzheimer's Disease", Biol. Psychiatry, May 2005, vol. 57, pp. 1052-1060.
Crawford et al., "Distinguishing between impairments of working memory and inhibitory control in cases of early dementia", Neuropsychologia, Dec. 2015, vol. 81, pp. 61-67.
Bott et al., "Web Camera Based Eye Tracking to Assess Visual Memory on a Visual Paired Comparison Task", Frontiers in Neuroscience, Jun. 2017, vol. 11, pp. 1-9.
Oyama et al., "Novel Method for Rapid Assessment of Cognitive Impairment Using High Performance Eye-Tracking Technology", Scientific Reports, Sep. 2019, vol. 9, pp. 1-9.
Nakajima, "Cerebral corticobasal degeneration (CBD) medical care and care manual Ver. 2", Health and Labor Science Research Grants Intractable Disease Policy Research Project, Mar. 2017, vol. 28, pp. 1-40 (English translation provided).

* cited by examiner

| | Case characteristic data | Characteristics | Cases |
|---|---|---|---|
| 311 | First characteristic data | First characteristic: Viewpoints are continuously gathered in local part having one point as center (one-point gaze pattern). | Fronto-tempora dementia |
| 312 | Second characteristic data | Second characteristic: The percentage of viewpoints present in display area of correct-answer image is small. | Decrease in cognitive function |
| 313 | Third characteristic data | Third characteristic: No viewpoint is present in left half of image (unilateral spatial neglect). | Corticobasal degeneration |
| 314 | Fourth characteristic data | Fourth characteristic: Viewpoints are gathered in inducing image which induces visual hallucination of human face. | Dementia with Lewy bodies |
| 315 | Fifth characteristic data | Fifth characteristic: It is difficult to track moving object in video. | Degradation in cognitive function |
| 316 | Sixth characteristic data | Sixth characteristic: Viewpoint obtainment percentage (when viewpoints are present on display surface) is smaller than or equal to second threshold value. | Fronto-temporal dementia (* Invalidate other diagnostic processes when viewpoint obtainment percentage is smaller than or equal to first threshold value) |
| | ... | ... | ... |

COGNITIVE IMPAIRMENT DIAGNOSTIC APPARATUS AND COGNITIVE IMPAIRMENT DIAGNOSTIC PROGRAM

TECHNICAL FIELD

The present invention relates to a cognitive impairment diagnostic apparatus and cognitive impairment diagnostic program for diagnosing cognitive impairment.

BACKGROUND ART

Conventionally, techniques related to cognitive impairment diagnostic apparatuses include techniques indicated below.

Patent Literature 1 and Patent Literature 2 have proposed a medical diagnostic apparatus using line of sight detection for detecting the head part of a subject and line of sight movements and objectively diagnosing a disease related to brain functions.

Patent Literature 3 proposes a system which detects eye-ball movements of a subject for diagnosing neural impairment.

Patent Literature 4 and Patent Literature 5 have proposed a chart for visual test for testing optic nerve impairment which appears in the case of a disease of an eye specifically a retina, an optic nerve, or the like, or an intracranial disease.

Patent Literature 6 to Patent Literature 9 have proposed an autism diagnosis supporting system which diagnoses autism of a subject using a line of sight detection unit which includes at least an imaging camera unit.

Patent Literature 10 has proposed a brain dysfunction disease diagnosis supporting apparatus which detects a line of sight and pupils of a subject, and determines whether the subject has a brain disease.

CITATION LIST

Patent Literature

[PTL 1] Japanese Unexamined Patent Application Publication No. H6-70884
[PTL 2] Japanese Unexamined Patent Application Publication No. H6-70885
[PTL 3] Japanese Unexamined Patent Application Publication (Translation of PCT Application) No. 2016-523112
[PTL 4] Japanese Patent Publication No. 4560801
[PTL 5] Japanese Patent Publication No. 4116354
[PTL 6] Japanese Patent Publication No. 5926210
[PTL 7] Japanese Patent Publication No. 5912351
[PTL 8] Japanese Patent Publication No. 5761048
[PTL 9] Japanese Patent Publication No. 5761049
[PTL 10] Japanese Patent Publication No. 5817582

SUMMARY OF INVENTION

Technical Problem

However, even if any of the above conventional techniques is used, it is difficult to provide a cognitive impairment diagnostic apparatus with convenience, low cost, objectivity, quantitativity, and versatility (language independence).

In Japan, it is reported that one of seven people aged 65 or above has dementia (approximately 4.4 million people), and that nearly 9 million elderly people including people in a pre-stage phase of dementia (that is, people with mild cognitive impairment) has some cognitive impairment. Furthermore, the number of patients with dementia in the world is expected to reach 132 million in 2050. The number of patients with dementia is supposed to be a triple of the current one.

The number of patients with dementia has been soaring recently as indicated above, it is desirable to achieve convenience, low cost, objectivity, quantitativity, and versatility in diagnosis by diagnostic apparatuses. Here, as for convenience, for example, it is desirable that a diagnosis can be completed in several minutes instead of requiring diagnosis time ranging from several tens of minutes to several hours. As for low cost, for example, it is desirable that no expensive dedicated apparatus be necessary, and maintenance and operating cost for a diagnostic apparatus be low. As for objectivity, it is desirable that a person who is involved in a diagnosis be not required to have much skill and experience, and thus that the person can make a consistent diagnosis. As for quantitativity, for example, it is desirable that the degree of dementia can be expressed as numerical values. As for versatility (language independence), it is desirable that a diagnosis can be made without depending on the kind of a language and without depending on a language even for an elderly person who does not have a sufficient conversation ability.

Even with the above conventional technique, it is difficult to achieve convenience, low cost, objectivity, quantitativity, and versatility in diagnosis by diagnostic apparatuses.

As current general diagnostic methods relating to cognitive impairment, initial diagnoses (screening) of dementia are based on neuropsychological test methods such as a Mini-Mental State Exam (MMSE). The MMSE is a cognitive function evaluation method in which an examiner asks questions to a subject, and has problems 1 to 4 indicated below. 1. It takes much time for each test. Specifically, it takes approximately 30 minutes. 2. A trained examiner is required for accurate evaluation. 3. A subject urged to answer the questions has much mental stress. 4. Results vary depending on examiners in most cases, and thus the reproducibility and objectivity are low.

A patient suspected to have dementia by screening is to be subjected to detailed testing in speciality outpatient clinic, etc. Principal objects here are to make a definitive diagnosis of dementia and to identify the cause disease thereof.

Various kinds of cause diseases of dementia have been known (in addition to most frequent Alzheimer's disease, fronto-temporal dementia, dementia with Lewy bodies, etc,). Courses of treatment vary between the cause diseases, and thus it is important to accurately discriminate a current cause disease from the other cause diseases. Discrimination between cause diseases of dementia depend on, for example, clinical symptom evaluations by medical specialists (characteristic clinical history, presence/absence of neurological findings, etc.) and special image evaluations (head MRI, PET image test, etc.), and thus has problems of quantitativity, cost, convenience, etc.

Since the number of patients with dementia is expected to soar as described above, in the future, it is important to develop a disease discrimination method or a supplemental diagnostic method which does not require medical specialists or special image diagnoses.

Furthermore, in the future, the numbers of elderly people in developing countries are expected to increase explosively in addition to long-lifespan developed countries such as Japan. Thus, early diagnoses of dementia and early intervention to dementia for these people are very important.

In view of this, it is important to establish a standard diagnostic approach which makes it possible to evaluate cognitive functions without intervention of particular languages.

At present, no cognitive impairment diagnostic apparatus provided with such convenience, low cost, objectivity, quantitativity, versatility (language independence) has been developed.

In view of this, the present invention has an object to provide a cognitive impairment diagnostic apparatus and a cognitive impairment diagnostic program provided with convenience, low cost, objectivity, quantitativity, versatility (language independence) in diagnosis of cognitive impairment.

Solution to Problem

A cognitive impairment diagnostic apparatus according to an aspect of the present invention includes: a display which displays a video for diagnosis of cognitive impairment on a display surface; an imaging unit configured to capture images of an eye of a subject; a detection unit configured to detect viewpoints of the subject on the display surface in time series based on the images captured by the imaging unit; a creation unit configured to create a distribution map representing a distribution of the viewpoints detected by the detection unit; a storage unit configured to store case characteristic data indicating a characteristic of a viewpoint distribution corresponding to a typical case in cognitive impairment; and a diagnostic unit configured to diagnose cognitive impairment of the subject by determining whether the distribution map has the characteristic indicated by the case characteristic data.

A cognitive impairment diagnostic program according to an aspect of the present invention is for use in a computer which is connected to an imaging unit and a display including a display surface and includes a storage unit which stores case characteristic data indicating characteristics of viewpoint distributions corresponding respectively to typical cases in cognitive impairment. The program causes the computer to execute: displaying a video for diagnosis of cognitive impairment on a display surface; capturing images of an eye of a subject, the capturing being performed by the imaging unit; detecting viewpoints of the subject on the display surface in time series based on the images captured by the imaging unit; creating a distribution map representing a distribution of the viewpoints detected; and diagnosing cognitive impairment of the subject by determining whether the distribution map has the characteristic indicated by the case characteristic data.

Advantageous Effects of Invention

A cognitive impairment diagnostic apparatus and a cognitive impairment diagnostic program according to an aspect of the present invention can be provided with convenience, low cost, objectivity, quantitativity, versatility (language independence) in diagnosis of cognitive impairment.

BRIEF DESCRIPTION OF DRAWINGS

FIG. 4 is a diagram illustrating one example of case characteristic data according to the embodiment.

DESCRIPTION OF EMBODIMENT

Hereinafter, an embodiment is described in detail with reference to the drawings.

It is to be noted that each of the exemplary embodiments described below indicates a generic or specific example. The numerical values, shapes, materials, constituent elements, the arrangement and connection of the constituent elements, steps, the processing order of the steps etc. indicated in the following exemplary embodiments are mere examples, and therefore do not limit the scope of the appended Claims. In addition, among the constituent elements in the following exemplary embodiments, constituent elements not recited in any one of the independent claims that define the most generic concept are described as optional constituent elements.

Each of the drawings is a schematic diagram, and thus is not always illustrated precisely. In each of the drawings, the same constituent elements are assigned with the same numerical signs.

EMBODIMENT

Hereinafter, a cognitive impairment diagnostic apparatus and a cognitive impairment diagnostic program according to an embodiment are described with reference to the drawings.

[1. Configuration of Cognitive Impairment Diagnostic Apparatus]

Figure 1:
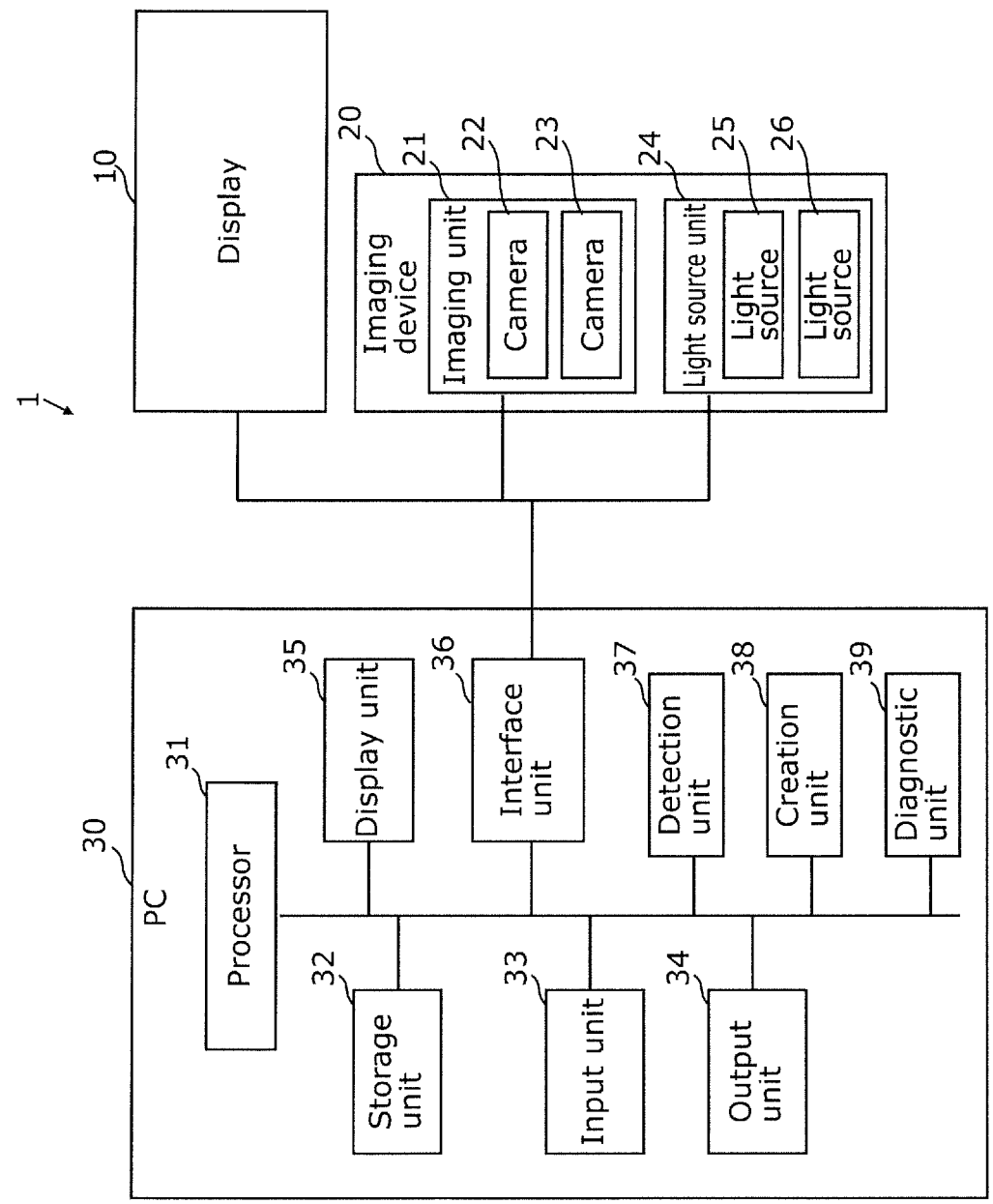
FIG. 1 is a block diagram illustrating a configuration example of a cognitive impairment diagnostic apparatus according to an embodiment.
Figure 2:
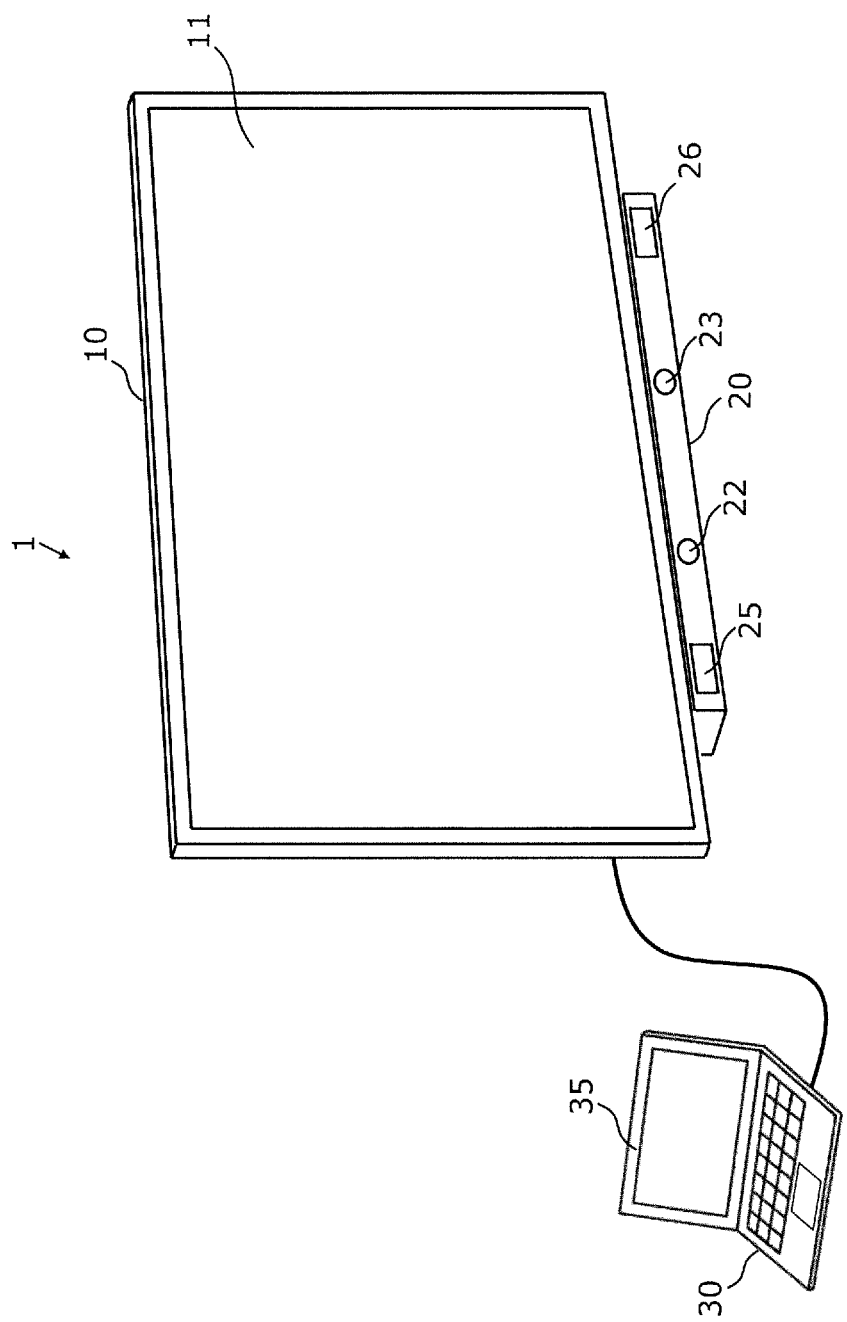
FIG. 2 is a diagram illustrating an appearance of the cognitive impairment diagnostic apparatus according to the embodiment.

FIG. 1 is a block diagram illustrating a configuration example of a cognitive impairment diagnostic apparatus according to the embodiment. FIG. 2 is a diagram illustrating an example of an appearance of the cognitive impairment diagnostic apparatus according to the embodiment.

As illustrated in FIG. 1, cognitive impairment diagnostic apparatus 1 includes display 10, imaging device 20, and personal computer (PC) 30. Cognitive impairment diagnostic apparatus 1 is a configuration example in which commercially-available general PC 30 is used as a main control device, and display 10 and imaging device 20 are added to PC 30.

Display 10 is a flat panel type display having display surface 11, and displays videos for diagnosis of cognitive impairment on display surface 11. As illustrated in FIG. 2, display 10 is a liquid crystal display or an organic EL display which is large enough for elderly people to watch videos for diagnosis, for the purpose of causing subjects to watch the videos for diagnosis. It is to be noted that display 10 may be a monitor for personal computers, or may be a monitor for commercially-available large TVs. Alternatively, display 10 may be configured with a screen as display surface 11 and a projector, instead of a flat panel type display.

Imaging device 20 is a module attachable to display 10, and includes at least imaging unit 21 for capturing images of eyes of a subject and light source unit 24.

Imaging unit 21 is a stereo camera including camera 22 and camera 23. Each of camera 22 and camera 23 may be, for example, an infrared camera. In another example, each of camera 22 and camera 23 may be, for example, a visible light camera. Alternatively, imaging unit 21 may include a single camera instead of being a stereo camera, or may include three or more cameras.

Light source unit 24 includes light source 25 and light source 26 which irradiate a subject with infrared rays as illumination light. For example, each of light source 25 and light source 26 may be configured to include one or more infrared light emitting diodes (LEDs). In another example, each of light source 25 and light source 26 may be one or more white light emitting diodes (LEDs). It is to be noted that imaging device 20 does not always need to include light source unit 24 when a subject is in a sufficiently bright illumination environment. Imaging device 20 may be attached to a top part of display 10, or may be divided into two components and the two components may be attached to right and left parts of display 10.

PC 30 includes processor 31, storage unit 32, input unit 33, output unit 34, display unit 35, interface unit 36, detection unit 37, creation unit 38, and diagnostic unit 39. Among the functional blocks illustrated in FIG. 1, processor 31, storage unit 32, input unit 33, output unit 34, display unit 35, and interface unit 36 may be configured with general hardware and software of commercially-available computers. The other functional blocks that are detection unit 37, creation unit 38, and diagnostic unit 39 are constituent elements which are implemented mainly by processor 31 executing the cognitive impairment diagnostic program according to this embodiment.

Processor 31 is what is called a central processing unit (CPU) which executes a program stored in storage unit 32.

Storage unit 32 stores the program which is executed by processor 31 and data which is processed by processor 31. Programs which are stored in storage unit 32 includes the cognitive impairment diagnostic program according to this embodiment in addition to various kinds of firmware, an operating system (OS), software such as driver software, etc. Data which is stored in storage unit 32 includes video data for diagnosis, case characteristic data, viewpoint data, distribution map data, etc. The video data for diagnosis is a still image or a video created for diagnosis of cognitive impairment. The case characteristic data is data indicating a characteristic of a viewpoint distribution corresponding to each of typical cases of cognitive impairment. The viewpoint data is time-series data indicating the positions and time points of viewpoints detected by detection unit 37. The distribution map is created by creation unit 38 plotting time-series viewpoints on a two-dimensional plane sequentially in real time according to viewpoint data, and indicates a two-dimensional distribution of the viewpoints.

Storage unit 32 include: a main memory or a primary memory configured with a Dynamic Random Access Memory (DRAM); a supplemental memory or a secondary memory configured with a Hard Disc Drive (HDD) or a Solid State Drive (SSD); and a cache memory. In other words, storage unit 32 here is used as a generic name of constituent elements having a function for storing the program and data.

Input unit 33 includes, for example, keyboards, a mouse, a track pad, etc., and receives an operation by an operator.

Output unit 34 is, for example, a speaker, and outputs sounds.

Display unit 35 is, for example, a liquid crystal display, and displays, for example, videos for diagnosis on which a distribution map is superimposed for monitoring by a user (examiner here).

Interface unit 36 has a function for connecting to display 10 and imaging device 20 via a cable and communicates therewith. Interface unit 36 is, for example, a High-Definition Multimedia Interface (HDMI, registered trademark) port and a Universal Serial Bus (USB) port. In this case, interface unit 36 connects display 10 via the HDMI (registered trademark) cable, and connects imaging unit 21 and light source unit 24 via the USB cable.

Detection unit 37 detects subject's viewpoints on display surface 11 in time series, based on images captured by imaging unit 21. For example, detection unit 37 detects subject's line of sight from the images captured by imaging unit 21, and detects pairs of coordinates on display surface 11 to which the line of sight is directed as the positions of the subject's viewpoints on display surface 11. The positions of viewpoints are cyclically detected. A cycle may be determined between several tens of milliseconds and several hundreds of milliseconds, and may be for example 100 mS. For example, detection unit 37 creates sets of coordinate data (x, y, t) including time points in real time as viewpoint data representing the positions of time-series viewpoints. Here, x and y are coordinates on a plane (for example, display surface 11 or a video for diagnosis), and t is a time point.

Creation unit 38 creates a distribution map indicating a distribution of the viewpoints detected by detection unit 37. The distribution map is, for example, a diagram obtained by plotting marks (for example, coloured dots) corresponding to the above coordinate data (x, y, t) on a two-dimensional plane. The distribution map is superimposed in real time on a video for diagnosis which is displayed in display unit 35 of PC 30. For example, a newer viewpoint among the above marks may be displayed brighter.

Diagnostic unit 39 diagnoses cognitive functions of the subject by determining whether the distribution map has a characteristic included in case characteristic data.

As described above, cognitive impairment diagnostic apparatus 1 illustrated in FIG. 1 includes: display 10 which displays a video for diagnosis of cognitive impairment on display surface 11; imaging unit 21 which captures images of an eye of a subject; detection unit 37 which detects viewpoints of the subject on display surface 11 in time series based on the images captured by imaging unit 21; creation unit 38 which creates a distribution map representing a distribution of the viewpoints detected by detection unit 37; storage unit 32 which stores case characteristic data 310 indicating a characteristic of a viewpoint distribution corresponding to a typical case in cognitive impairment; and diagnostic unit 39 which diagnoses cognitive impairment of the subject by determining whether the distribution map has the characteristic indicated by case characteristic data 310.

With this configuration, in diagnosis of cognitive function by cognitive impairment diagnostic apparatus 1, it is possible to achieve convenience, low cost, objectivity, quantitativity, and versatility (language independence).

It is to be noted that PC 30 illustrated in FIG. 1 and FIG. 2 may be a laptop computer or a desk-top computer.

[1.1 Program and Data in Storage Unit 32]

Next, programs and data which are stored in storage unit 32 are described.

Figure 3:
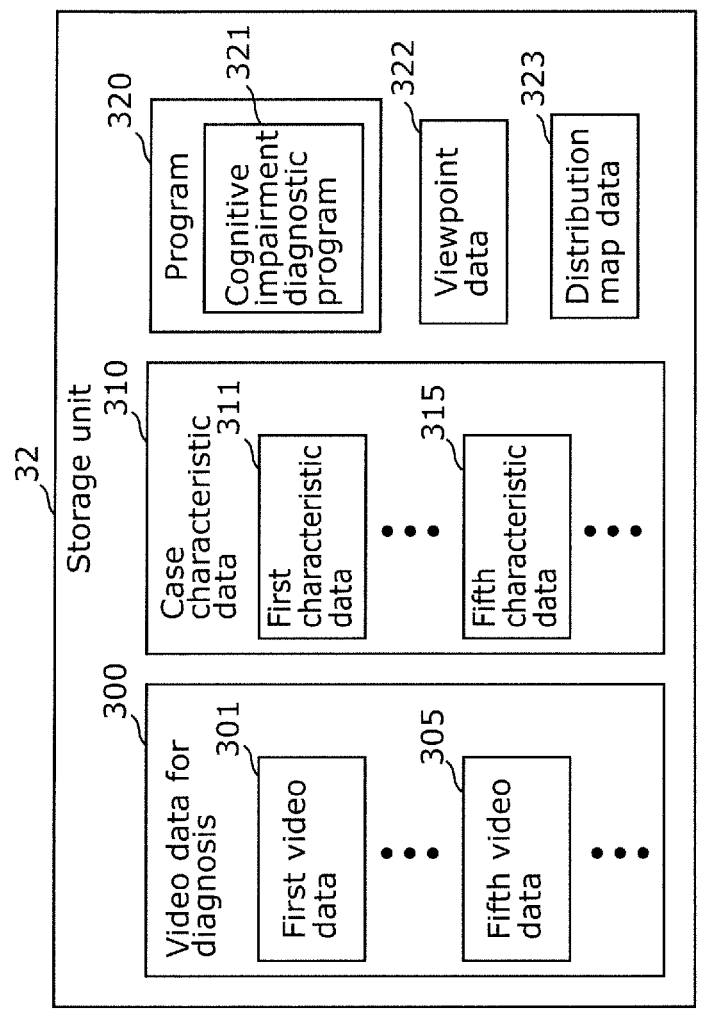
FIG. 3 is a diagram illustrating one example of content stored in a storage unit according to the embodiment.

FIG. 3 is a diagram illustrating one example of content stored in storage unit 32 according to the embodiment. In the diagram, storage unit 32 stores video data for diagnosis 300, case characteristic data 310, program 320, viewpoint data 322, and distribution map data 323. Program 320 includes cognitive impairment diagnostic program 321.

Video data for diagnosis 300 is a group of video data from first video data 301 to fifth video data 305. Each of the video data is a video created for diagnosing whether there is cognitive impairment or the degree of cognitive impairment, or a video created for discriminating a case from the other cases in cognitive impairment.

Case characteristic data 310 is data indicating a characteristic of a viewpoint distribution corresponding to each of typical cases of cognitive impairment, and is a group of characteristic data from first characteristic data 311 to fifth characteristic data 315. First characteristic data 311 to fifth characteristic data 315 correspond respectively to first video data 301 to fifth video data 305.

Program 320 includes various kinds of firmware, an operating system (OS), software such as driver software, and cognitive impairment diagnostic program 321. Cognitive impairment diagnostic program 321 is a program executed by a computer that is PC 30, and causes the computer to diagnose a cognitive impairment of a subject by: displaying a video for diagnosis of cognitive impairment on display surface 11; capturing images of an eye of a subject by imaging unit 21; detecting viewpoints of the subject on display surface 11 in time series based on the images captured by imaging unit 21; creating a distribution map representing a distribution of the viewpoints detected; and diagnosing cognitive impairment of the subject by determining whether the distribution map has the characteristic indicated by the case characteristic data. Detecting the subject's viewpoints on display surface 11 in time series by PC 30 based on the images captured by imaging unit 21 is a function of detection unit 37. Creating the distribution map indicating the distribution of the viewpoints detected is a function of creation unit 38. Diagnosing the cognitive impairment of the subject by determining whether the distribution map has the characteristic in the case characteristic data is a function of diagnostic unit 39.

Viewpoint data 322 is time-series data indicating the positions and time points of the viewpoints detected by detection unit 37, and is, for example, sets of coordinate data (x, y, t) including the time points already described.

Distribution map data 323 is data indicating the distribution map already described.

It is to be noted that storage unit 32 stores the program and data indicated in FIG. 3, and also stores diagnostic data indicating results of diagnoses of subjects, viewpoint data 322 for each subject, and data which associates distribution map data 323 and the diagnostic data.

Subsequently, specific examples of case characteristic data 310 are described.

FIG. 4 is a diagram illustrating one example of case characteristic data 310 according to the embodiment. Case characteristic data 310 in the diagram includes first characteristic data 311 to sixth characteristic data 316. The diagram indicates each of first characteristic data 311 to sixth characteristic data 316 and a corresponding case in cognitive impairment.

First characteristic data 311 associates a first characteristic with fronto-temporal dementia. Fronto-temporal dementia may be abbreviated as FTD. The first characteristic is a typical case characteristic of a patient with fronto-temporal dementia. Specifically, the first characteristic indicates a characteristic that viewpoints are continuously gathered in a local part having one point as a center. This first characteristic may be referred to as one-point gaze pattern. The first characteristic is obtainable on a precondition that a first video which is a video for diagnosis based on first video data 301 is presented to a subject. In this case, the first video may be, for example, an image of at least one of a person, an object, a landscape, or a graphic symbol.

Second characteristic data 312 associates a second characteristic with a decrease in cognitive function. In other words, the second characteristic is a typical characteristic of a patient with the decrease in cognitive function. More specifically, the second characteristic indicates a characteristic that a cognitive function is lower as the percentage of subject's viewpoints present in a display area of a correct-answer graphic symbol in a distribution map is smaller. The second characteristic is obtainable on a precondition that a second video which is a video for diagnosis based on second video data 302 is presented to the subject. In this case, the second video may be a video including: a first image which includes a correct-answer graphic symbol and does not include any graphic symbol other than the correct-answer graphic symbol; and a second image which includes the correct-answer graphic symbol and a plurality of similar graphic symbols. The second image is displayed immediately after the first image is displayed. The distribution map is a distribution of viewpoints of the subject who is looking at the second image.

Third characteristic data 313 associates a third characteristic with corticobasal degeneration. More specifically, third characteristic is a typical characteristic of a patient with corticobasal degeneration. More specifically, the third characteristic indicates a characteristic that no viewpoint is present in the left half of an image, in other words, the unilateral space is neglected. The third characteristic is obtainable on a precondition that a third video which is a video for diagnosis based on third video data 303 is presented to the subject. In this case, the third video may be, for example, an image of at least one of a person, an object, a landscape, or a graphic symbol.

Fourth characteristic data 314 associates a fourth characteristic with dementia with Lewy bodies. In other words, the fourth characteristic is a typical characteristic of a patient with dementia with Lewy bodies. More specifically, the fourth characteristic indicates a characteristic that viewpoints are gathered in an inducing image which induces visual hallucination visual hallucination of a human face. The fourth characteristic is obtainable on a precondition that a fourth video which is a video for diagnosis based on fourth video data 304 is presented to the subject. In this case, the fourth video may be a still image including both the inducing image and a plurality of non-inducing images which do not induce visual hallucination of a human face.

Fifth characteristic data 315 associates a fifth characteristic with a decrease in cognitive function. In other words, the fifth characteristic is a typical characteristic of a patient with the decrease in cognitive function. More specifically, the fifth characteristic indicates a characteristic that it is difficult for the eyes of a patient to track a moving object in a video. The fifth characteristic is obtainable on a precondition that a fifth video which is a video for diagnosis based on fifth video data 305 is presented to the subject. In this case, the fifth video may be, for example, a video of a moving object in display surface 11.

Sixth characteristic data 316 associates a sixth characteristic with fronto-temporal dementia. In other words, the sixth characteristic is a typical characteristic of a patient with fronto-temporal dementia. More specifically, the sixth characteristic indicates a characteristic that a viewpoint obtainment percentage is smaller than or equal to a predetermined value (this predetermined value is referred to as a second threshold value th2). Here, the viewpoint obtainment percentage is a percentage of viewpoints present in display surface 11 in a distribution map. The sixth characteristic is obtainable on a precondition that an optional video for diagnosis is presented to the subject. This video for diagnosis may be used as one or all of the first video to fifth video.

The viewpoint obtainment percentage is an indicator indicating validity of a diagnosis of cognitive impairment by cognitive impairment diagnostic apparatus 1. In other words, when the percentage of the viewpoints present outside display surface 11 in the distribution map is large, it is impossible to guarantee the validity of the result of the diagnosis of cognitive impairment based on characteristic data other than sixth characteristic data 316 by cognitive impairment diagnostic apparatus 1. In view of this, the result of the diagnosis made based on the characteristic data other than sixth characteristic data 316 is invalidated when the viewpoint obtainment percentage is smaller than or equal to a predetermined value (this predetermined value is referred to as threshold value th1), and the result of the diagnosis made by cognitive impairment diagnostic apparatus 1 is validated when the viewpoint obtainment percentage is larger than the first threshold value. When the viewpoint obtainment percentage is represented as a value ranging from 0 to 1, for example, first threshold value th1 is 0.8. In addition, second threshold value th2 may be the same value as first threshold value th1.

[1.2 Operation Performed by Cognitive Impairment Diagnostic Apparatus 1]

Descriptions are given of operations performed by cognitive impairment diagnostic apparatus 1 configured as described above according to the embodiment.

Figure 5:
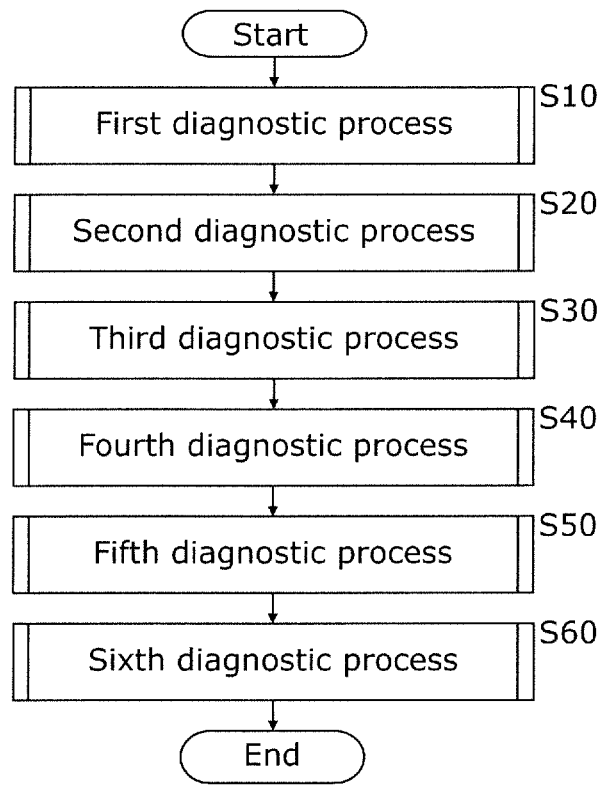
FIG. 5 is a flow chart indicating diagnostic processing performed by the cognitive impairment diagnostic apparatus according to the embodiment.
Figure 6:
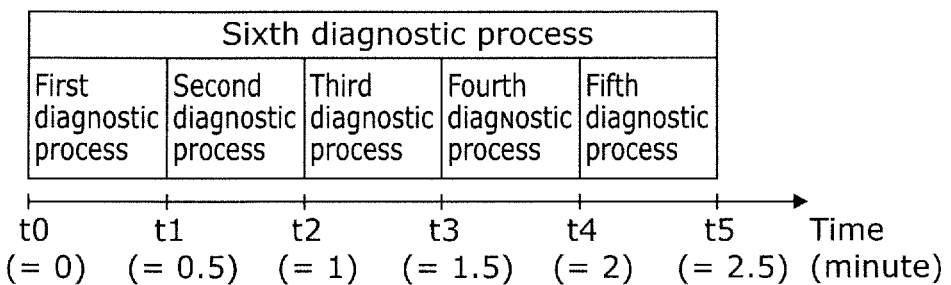
FIG. 6 is a diagram indicating one example of time required for the diagnostic processing in FIG. 5.

FIG. 5 is a flow chart indicating an example of diagnostic processing performed by cognitive impairment diagnostic apparatus 1 according to the embodiment. FIG. 6 is a diagram indicating one example of time required for the diagnostic processing in FIG. 5.

As illustrated in FIG. 5 and FIG. 6, cognitive impairment diagnostic apparatus 1 sequentially executes a first diagnostic process (S10) to a fifth diagnostic process (S50). It is to be noted that a sixth diagnostic process is executed in parallel with the first diagnostic process to the fifth diagnostic process as illustrated in FIG. 6. The examples of the diagnostic processes in FIG. 5 and FIG. 6 are processes which are realized mainly by PC 30 executing cognitive impairment diagnostic program 321. In addition, each of time points t0 to t5 in FIG. 6 indicates corresponding one or more of start time points and end time points of the diagnostic processes. In FIG. 6, time points t0 to t5 are evenly apart at 0.5 minute (30 seconds) intervals.

The first diagnostic process is a diagnostic process using first video data 301 and first characteristic data 311. The second diagnostic process is a diagnostic process using second video data 302 and second characteristic data 312. The third diagnostic process is a diagnostic process using third video data 303 and third characteristic data 313. The fourth diagnostic process is a diagnostic process using fourth video data 304 and fourth characteristic data 314. The fifth diagnostic process is a diagnostic process using fifth video data 305 and fifth characteristic data 315. The sixth diagnostic process is a diagnostic process using sixth video data 316. In addition, distribution map data 323 includes a first distribution map to a fifth distribution map corresponding respectively to a first video to a fifth video.

In FIG. 6, a time duration of each of the first diagnostic process to the fifth diagnostic process is 0.5 minute. The time duration of the sixth diagnostic process is 2 minutes and 30 seconds because the sixth diagnostic process is performed in parallel with the first diagnostic process to the fifth diagnostic process. In the diagram, the time required for the six diagnostic processes from the first diagnostic process to the sixth diagnostic process is approximately 2 minutes and 30 seconds. Although a cognitive impairment diagnostic method using a currently-used general MMSE in which an examiner asks questions to a subject takes approximately 30 minutes, cognitive impairment diagnostic apparatus 1 reduces time required for a plurality of diagnostic processes significantly compared with the method using the MMSE.

It is to be noted that the time duration of each of the first diagnostic process to the fifth diagnostic process does not always need to be 0.5 minute (30 seconds), and may be determined within a range from approximately 10 seconds to several tens of seconds. In addition, the total processing time duration from the first diagnostic process to the sixth diagnostic process may be determined to be several minutes or below, for example, 3 minutes or below.

In addition, when a subject does not at all exhibit a decrease in cognitive function in each of the first diagnostic process to the fifth diagnostic process and thus a subject is determined to be cognitively healthy, the processes may be finished without being fully performed.

It is to be noted that the order of the first diagnostic process to the fifth diagnostic process may be another order different from the one in FIG. 5 and FIG. 6. For example, the first diagnostic process, the third diagnostic process, and the fourth diagnostic process in which a case of cognitive impairment can be discriminated from the other cases may be executed after the second diagnostic process and the fifth diagnostic process in which a decrease in cognitive function is diagnosed is executed.

In addition, in FIG. 5 and FIG. 6, at least one of the first diagnostic process to the sixth diagnostic process may be selected and executed. As one example, the second diagnostic process and the fifth diagnostic process in which a decrease in cognitive function is diagnosed may be selected and executed. As another example, the first diagnostic process, the third diagnostic process, and the fourth diagnostic process in which a case of cognitive impairment can be discriminated from the other cases may be selected and executed. As still another example, any one of the first diagnostic process to the sixth diagnostic process may be selected and executed. As still another example, the second diagnostic process and the fifth diagnostic process in which a decrease in cognitive function is diagnosed and the sixth diagnostic process in which the validity of each of the diagnostic processes is also determined may be executed, and when a decrease in cognitive function is diagnosed, the remaining first diagnostic process, third diagnostic process, and fourth diagnostic process may be executed.

It is to be noted that a calibration process for viewpoint detection may be performed before the examples of the diagnostic processes in FIG. 5 and FIG. 6 are started.

[1.2.1 First Diagnostic Process]

Next, the first diagnostic process is described in detail. The first diagnostic process uses the above-described first characteristic. In other words, the first diagnostic process uses a characteristic that a patient with fronto-temporal dementia exhibits one-point gaze pattern in which the patient keeps gazing one point.

Figure 7:
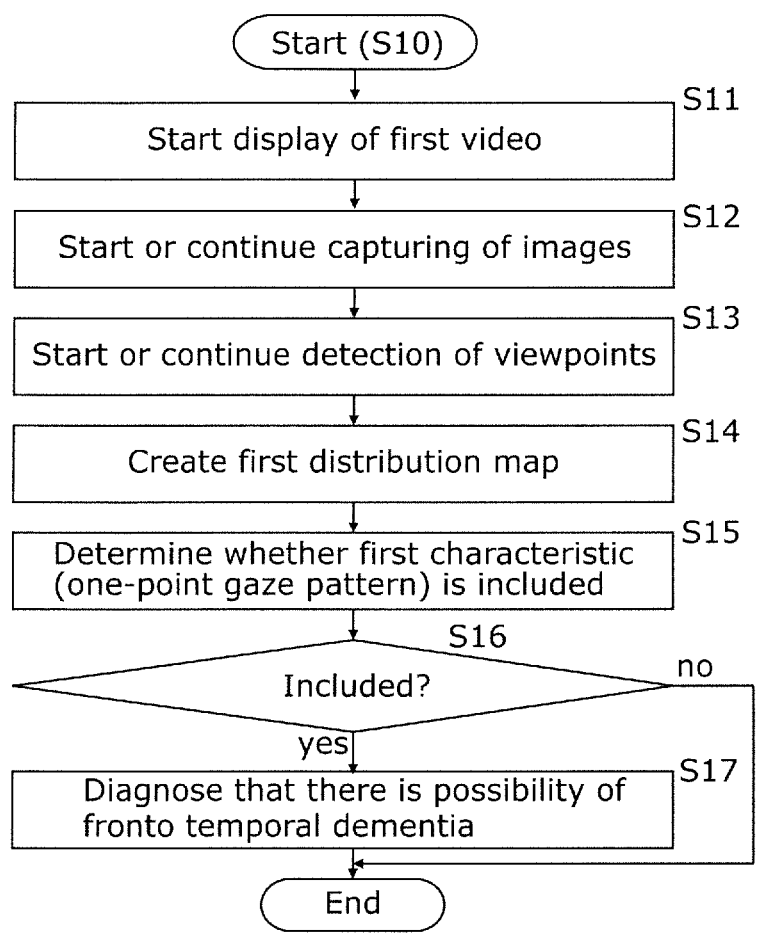
FIG. 7 is a flow chart indicating one example of a first diagnostic process in FIG. 5.

FIG. 7 is a flow chart indicating one example of a first diagnostic process (S10) in FIG. 5. As illustrated in FIG. 7, first, PC 30 reads out first video data 301 from storage unit 32, and starts to display a first video indicated by first video data 301 in display 10 (S11).

Figure 13A:
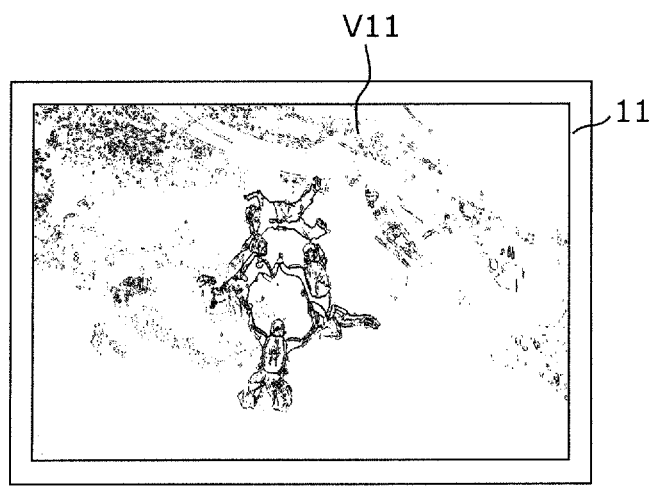
FIG. 13A is a diagram illustrating a display example of a first video according to the embodiment.

FIG. 13A is a diagram illustrating a display example of a first video according to the embodiment. In FIG. 13A, image V11 is displayed on display surface 11. Image V11 is a captured image of people who are doing sky diving and the ground. Although image V11 is represented as a line drawing in FIG. 13A for convenience, image V11 may be actually a full-colour image.

PC 30 displays image V11 as in FIG. 13A during a time duration from time points t0 to t1 in FIG. 6. Alternatively, another image may be displayed after image V11 as in FIG. 13A is displayed.

Furthermore PC 30 causes imaging unit 21 to start to capture images of eyes of a subject or to continue performing ongoing image capturing (S12), and to start to detect viewpoints of the subject or to continue performing ongoing viewpoint detection (S13).

Furthermore, PC 30 obtains viewpoint data from detection unit 37 from start to end of display of the first video, and creates a first distribution map corresponding to the first video in real time (S14), displays the first video in display unit 35, and superimposes the first distribution map on the first video in display unit 35. The following processes are executed in parallel: display of the first video in display 10 and display unit 35; image capturing by imaging unit 21; viewpoint detection by PC 30 (specifically, detection unit 37 in FIG. 1); and creation of the first map by PC 30 (specifically, creation unit 38 in FIG. 1).

Subsequently, PC 30 determines whether the first distribution map includes a first characteristic included in case characteristic data (S15), and when the answer is positive (yes in S16), it is diagnosed that there is a possibility of fronto-temporal dementia (S17). The first characteristic is a one-point gaze pattern. A patient with fronto-temporal dementia is characterized by keeping gazing one point. In other words, the first characteristic indicates that viewpoints are gathered in a local part having the one point as a center.

Figure 13B:
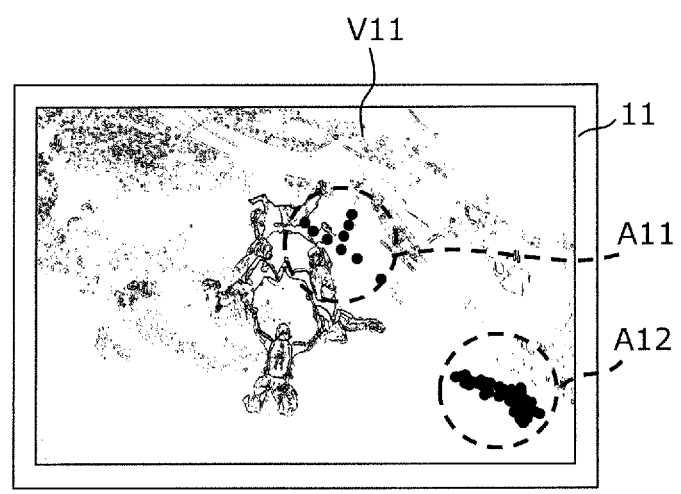
FIG. 13B is a diagram illustrating a display example obtained by superimposing a first distribution map on the first video in FIG. 13A.

FIG. 13B is a diagram illustrating a display example obtained by superimposing a first distribution map on the first video in FIG. 13A. FIG. 13B is a display example in display unit 35 in PC 30. The display example is obtained by superimposing the first distribution map on image V11 included in the first video when a patient with fronto-temporal dementia is a subject. In FIG. 13B, each of black circles represents a detected single viewpoint. Few viewpoints among the viewpoints are present in broken-line frame A11, and an overwhelming majority of the viewpoints is present in broken-line frame A12. This first distribution map includes a characteristic of one-point gaze pattern in broken-line frame A12.

As described above, in the first diagnostic process: the video for diagnosis includes image V of at least one of a person, an object, a landscape, or a graphic symbol; case characteristic data 310 indicates a one-point gaze pattern in which viewpoints are continuously gathered in a local part having one point as a center; and diagnostic unit 39 diagnoses that there is a possibility of fronto-temporal dementia included in cognitive impairment when the distribution map has the characteristic.

In this way, the first diagnostic process makes it possible to discriminate fronto-temporal dementia from the other cases in cognitive impairment in a simple and easy way. Furthermore, the first diagnostic process can be executed in short time of several tens of seconds, and thus can achieve convenience, low cost, objectivity, quantitativity, and versatility (language independence).

[1.2.2 Second Diagnostic Process]

Next, the second diagnostic process is described in detail. The second diagnostic process is a diagnostic process of cognitive impairment by graphic symbol pattern matching using the second characteristic. In other words, the second diagnostic process is for diagnosing a decrease in cognitive function by presenting a particular graphic symbol, then presenting a correct-answer graphic symbol (that is the particular graphic symbol presented firstly) together with a plurality of different graphic symbols, and evaluating how much the subject gazes the correct-answer graphic symbol.

Figure 8:
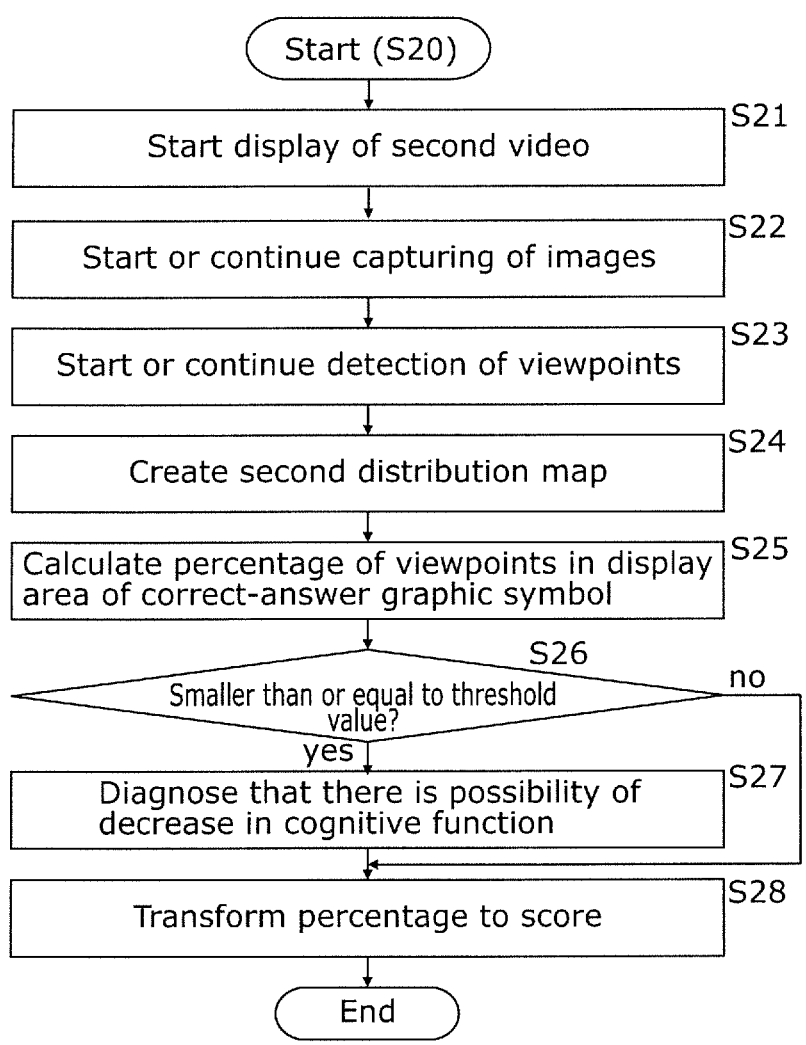
FIG. 8 is a flow chart indicating one example of a second diagnostic process in FIG. 5.

FIG. 8 is a flow chart indicating one example of a second diagnostic process (S20) in FIG. 5. As illustrated in FIG. 8, first, PC 30 reads out second video data 302 from storage unit 32, and starts to display a second video indicated by second video data 302 in display 10 (S21). The second video is a video including: a first image which includes a correct-answer graphic symbol and does not include any graphic symbol other than the correct-answer graphic symbol; and a second image which includes the correct-answer graphic symbol and a plurality of graphic symbols similar to the correct-answer graphic symbol. The second image is displayed immediately after the display of the first image is ended.

Figure 14A:
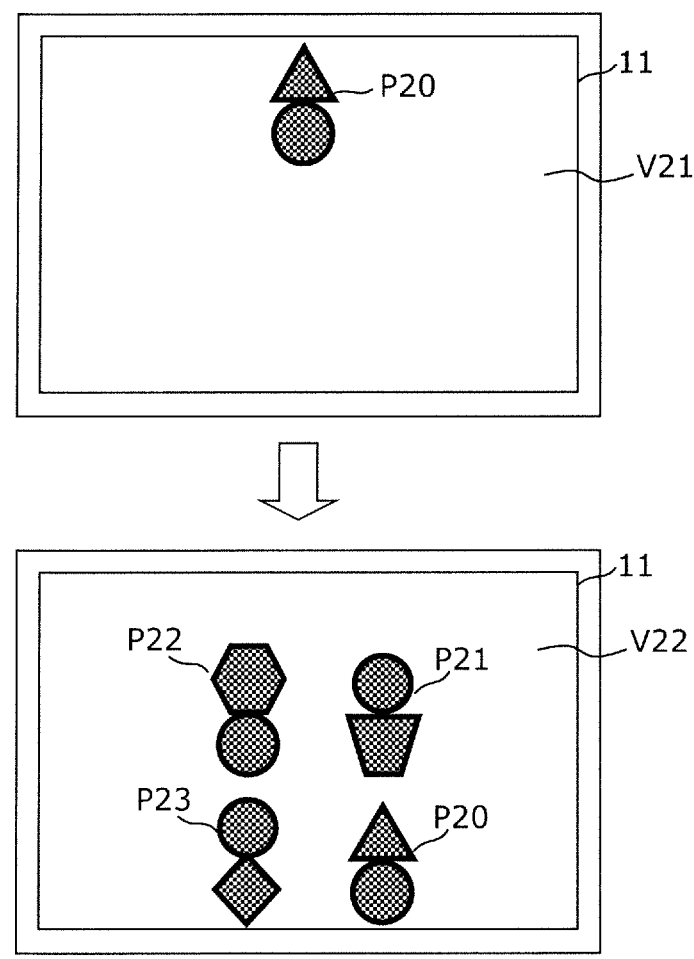
FIG. 14A is a diagram illustrating a display example of a second video according to the embodiment.

FIG. 14A is a diagram illustrating a display example of a second video according to the embodiment. The upper row in FIG. 14A is a display example of first image V21 displayed on display surface 11. First image V21 includes correct-answer graphic symbol P20, and does not include any other graphic symbol. It is to be noted that the correct-answer graphic symbol is a single graphic symbol which is presented firstly to a subject and is included in the first image displayed firstly in the second diagnostic process. The display time of first image V21 may range, for example, from 5 to 20 seconds. It is to be noted that the first image may include a message image which prompts the subject to memorize the correct-answer graphic symbol such as "Remember this graphic symbol well." In addition, PC 30 may repeatedly output a message voice of "Remember this graphic symbol well." to the subject together with the display of the first image. Furthermore, PC 30 may use both the message image and the message voice.

PC 30 further causes imaging unit 21 to start to capture images of eyes of the subject or to continue performing ongoing image capturing (S22), and to start to detect viewpoints of the subject or to continue performing ongoing viewpoint detection (S23). Furthermore, PC 30 obtains viewpoint data from detection unit 37 from start to end of display of the first video, and creates a second distribution map corresponding to the second video in real time (S24), displays the second video in display unit 35, and superimposes the second distribution map on the second video in display unit 35. At this time, PC 30 creates, as the second distribution map, each of a first partial map and a second partial map in real time. The first partial map indicates a distribution of viewpoints in a period during which a first image is being displayed, and the second partial map indicates a distribution of viewpoints in a period during which a second image is being displayed. In other words, the second distribution map includes two maps which are the first partial map and the second partial map. The following processes are executed in parallel: display of the second video in display 10 and display unit 35; image capturing by imaging unit 21; viewpoint detection by PC 30 (specifically, detection unit 37 in FIG. 1); and creation of the second map by PC 30 (specifically, creation unit 38 in FIG. 1).

The lower row in FIG. 14A is a display example of second image V22 displayed on display surface 11. Second image V22 includes similar graphic symbols P21, P22, and P23 in addition to correct-answer graphic symbol P20. Each of similar graphic symbols P21, P22, and P23 is a graphic symbol similar to the correct-answer graphic symbol, in other words, a graphic symbol that is partly identical to and partly different from the correct-answer graphic symbol. The display time of second image V22 may be, for example, 5 to 15 seconds. The second image may include a message image such as "Please gaze the graphic symbol identical to the previous graphic symbol." which prompts the subject to gaze the correct-answer graphic symbol. Alternatively, PC 30 may repeatedly output a message voice of "Please gaze the graphic symbol identical to the previous graphic symbol." or the like which prompts the subject to gaze the correct-answer graphic symbol while the second image is being displayed. Furthermore, PC 30 may use both the message image and the message voice.

Subsequently, PC 30 determines whether the second distribution map includes a second characteristic included in the case characteristic data. More specifically, PC 30 calculates the percentage of viewpoints present in a display area of the correct-answer graphic symbol in the second partial map, and determines whether the calculated percentage is smaller than or equal to a threshold value (S25). Furthermore, when the percentage is smaller than or equal to the threshold value (yes in S26), PC 30 diagnoses that there is a possibility of a decrease in cognitive function (S27). This threshold value may be, for example, 0.5 (that is, 50%). In addition, PC 30 normalizes the percentage of viewpoints present in the display area of the correct-answer graphic symbol to transform the percentage into a score (S28), and displays the score in display unit 35. For example, PC 30 may transform the percentage into a score based on a scale of 5. For example, the percentage may be transformed into: score 1 when the percentage is in a range from 0% to less than 20%; score 2 when the percentage is in a range from 20% to less than 40%; score 3 when the percentage is in a range from 40% to less than 60%; score 4 when the percentage is in a range from 60% to less than 80%; and score 5 when the percentage is in a range from 80% to less than 100%. As for the meaning of each score in the transformation into a score, for example, score 5 indicates a cognitively healthy subject. Score 4 indicates that a decrease in cognitive function is hardly seen, that is, score 4 indicates a cognitively healthy subject. Score 3 indicates that a decrease in cognitive function is seen a little, that is, a slight decrease in cognitive function is seen. In other words, score 3 indicates a subject is on a border line between dementia and cognitive health. Score 2 indicates that a small decrease in cognitive function is seen, that is, a subject is a patient with non-serious, early-stage dementia. Score 1 indicates that a decrease in cognitive function is large, that is, a subject is a patient with serious dementia.

Figure 14B:
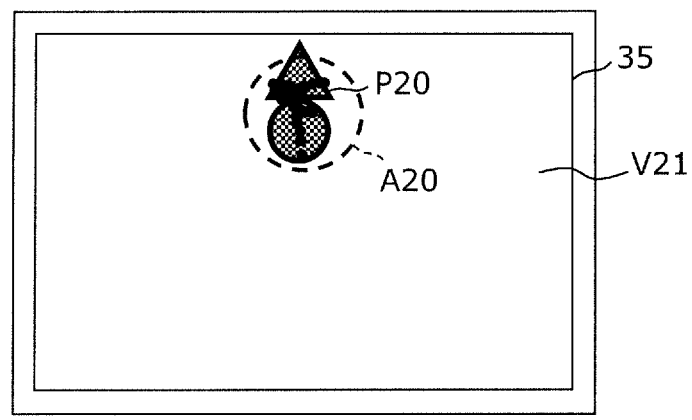
FIG. 14B is a diagram illustrating a display example obtained by superimposing a first partial map in a second distribution map onto a first image in the second video in FIG. 14A.

FIG. 14B is a diagram illustrating a display example obtained by superimposing a first partial map in a second distribution map onto first image V21 in the second video in FIG. 14A. FIG. 14B is a display example in display unit 35 of PC 30. In the diagram, each of black circles represents a detected single viewpoint. First image V21 in FIG. 14B prompts a subject to memorize correct-answer graphic symbol P20. In the diagram, as illustrated in broken-line frame A20, many viewpoints are gathered in the display area of correct-answer graphic symbol P20. Thus, it is known that the subject has gazed correct-answer graphic symbol P20 and has tried to memorize correct-answer graphic symbol P20.

Figure 14C:
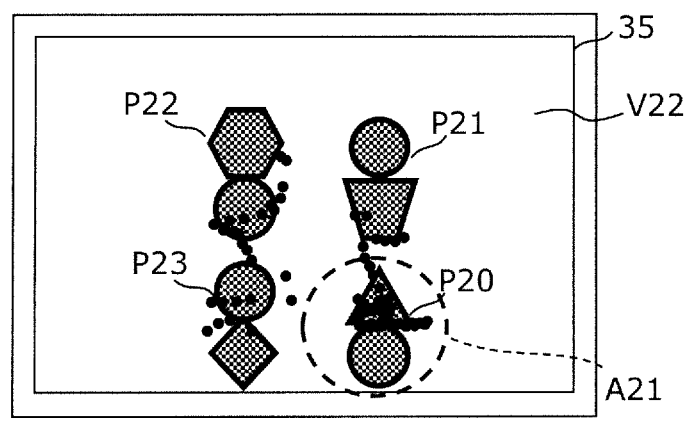
FIG. 14C is a diagram illustrating a display example obtained by superimposing a second partial map in a second distribution map of a cognitively healthy subject onto a second image in the second video in FIG. 14A.

FIG. 14C is a diagram illustrating a display example obtained by superimposing a second partial map in a second distribution map of a cognitively healthy subject onto second image V22 in the second video in FIG. 14A. The diagram illustrates a display example in display unit 35. As illustrated in broken-line frame A21 in the diagram, a larger number of viewpoints are present in the display area of correct-answer graphic symbol P20 than in the display areas of similar graphic symbols P21 to P23. In this example, the percentage of viewpoints present in the display area of the correct-answer graphic symbol is larger than or equal to a threshold value (for example, 50%). Thus, PC 30 is to determine that the answer is no in Step S26, and to calculate score 5 or score 4 on the scale of 5 in the transformation into a score in Step S28 without diagnosing that there is a possibility of a decrease in cognitive function.

Figure 14D:
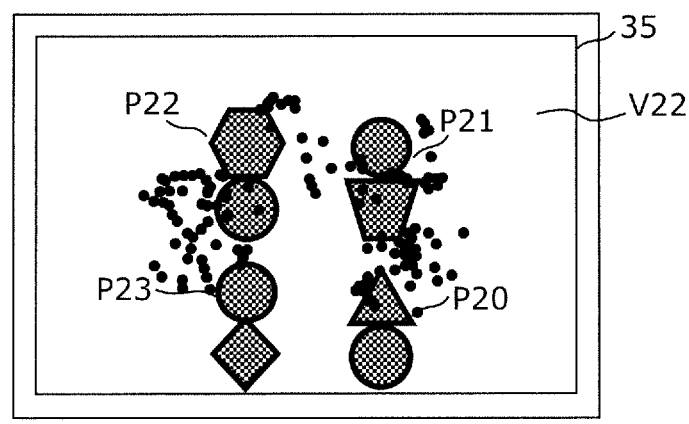
FIG. 14D is a diagram illustrating a display example obtained by superimposing a second partial map in a second distribution map of a patient with Alzheimer's disease onto a second image in the second video in FIG. 14A.

FIG. 14D is a diagram illustrating a display example obtained by superimposing a second partial map of a patient with Alzheimer's disease onto second image V22 in the second video in FIG. 14A. The diagram illustrates a display example in display unit 35. Compared with FIG. 14C, in FIG. 14D, viewpoints are randomly present in the display areas of correct-answer graphic symbol P20 and similar graphic symbols P21 to P23 without being gathered in the display area of correct-answer graphic symbol P20. In the example of FIG. 14D, the percentage of viewpoints present in the display area of correct-answer graphic symbol P20 is smaller than a threshold value (for example, 50%). Thus, PC 30 is to determine that the answer is yes in Step S26, to diagnose that there is a possibility of a decrease in cognitive function in Step S27, and to calculate score 1 or score 2 on the scale of 5 in the transformation into a score in Step S28.

Subsequently, scores in the transformation into a score in the second diagnostic process and scores a general MMSE are described in comparison.

Figure 18:
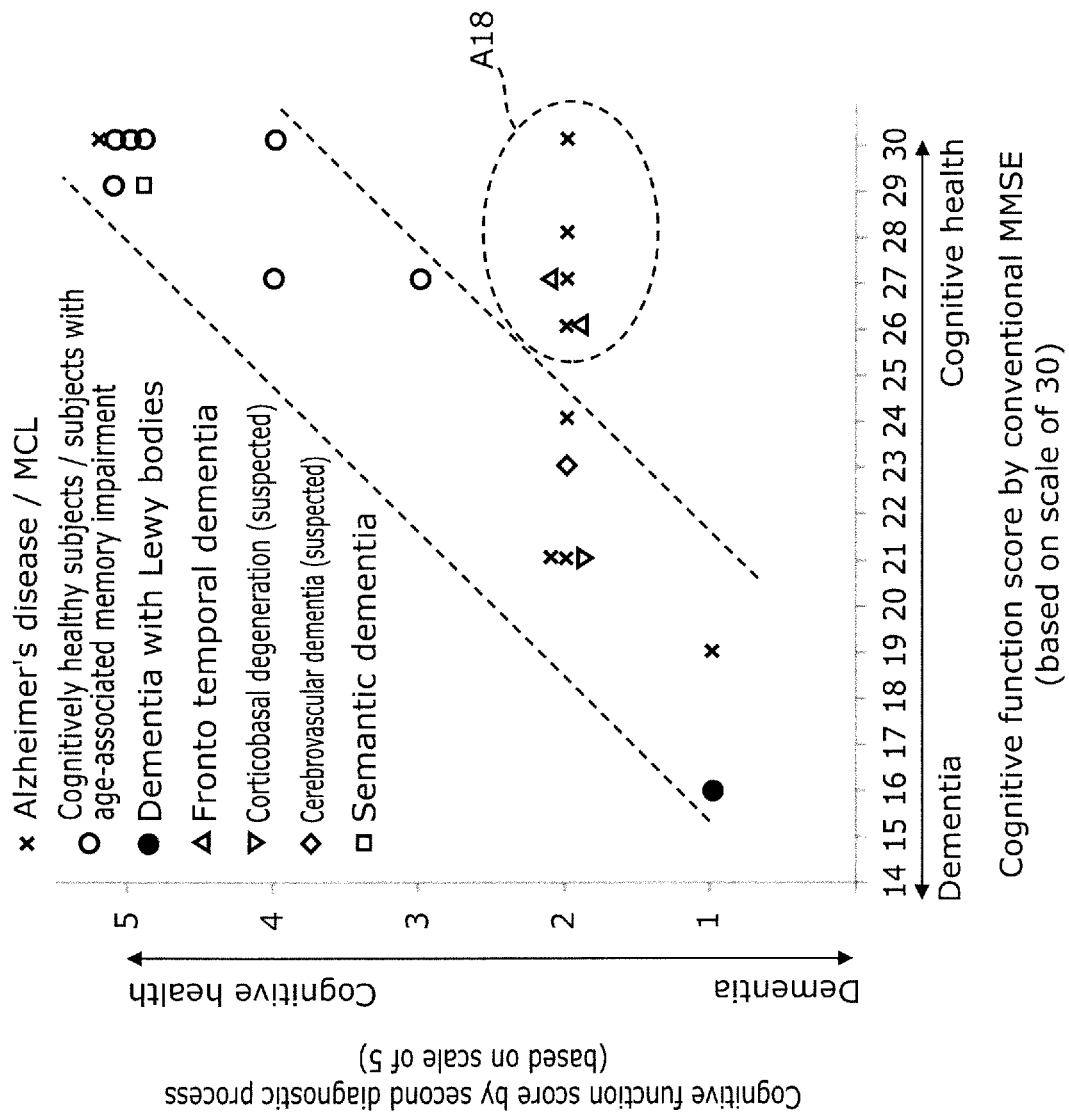
FIG. 18 is a diagram which compares cognitive function scores by the second diagnostic process according to the embodiment and cognitive function scores by a conventional MMSE method.

FIG. 18 is a diagram which compares cognitive function scores by the second diagnostic process according to the embodiment and cognitive function scores by the conventional MMSE method. In the diagram, the vertical axis indicates cognitive function scores in the second diagnostic process, which are scores on the scale of 5 in the transformation into a score in Step S28. The horizontal axis indicates cognitive function scores by the conventional MMSE. The cognitive function scores by the MMSE are on a scale of 30. Score 30 indicates a cognitively healthy subject. A lower score indicates a lower cognitive function.

The diagram indicates results obtained by causing each of approximately 20 subjects to undergo a second diagnostic process and receive a diagnosis by the MMSE. Whether the subject is with or without dementia and the disease type (cause disease) of each of patients among the subjects are known in advance. In the diagram, each of crosses indicates a subject with Alzheimer's disease or with mild cognitive impairment (MCI). Each of white circles indicates a cognitively healthy subject or a subject with age-associated memory impairment. A black circle indicates a subject with dementia with Lewy bodies. Each of upward triangles indicates a subject with fronto-temporal dementia. A downward triangle indicates a subject suspected to have corticobasal degeneration. A rhomboid indicates a subject suspected to have cerebrovascular dementia. A square indicates a subject with semantic dementia.

In FIG. 18, the cognitive function scores by the second diagnostic process and the cognitive function scores by the conventional MMSE method are roughly correlated with each other. In other words, it has been shown that the second diagnostic process makes it possible to evaluate cognitive functions of the subjects as in the conventional MMSE.

Furthermore, as illustrated in broken-line frame A18, it has been shown that the second diagnostic process makes it possible to detect patients with early-stage dementia although they are evaluated as cognitively healthy subjects by the MMSE because the subjects get a high cognitive score in MMSE. The subjects in broken-line frame A18 are diagnosed as patients with early-stage dementia by cerebrospinal fluid tests. In this way, it has been shown that the second diagnostic process makes it possible to diagnose cognitive impairment with a higher sensitivity than in the conventional MMSE.

As described above, in the second diagnostic process: the video for diagnosis is a video including a first image which includes correct-answer graphic symbol P20 and does not include any graphic symbol other than correct-answer graphic symbol P20; and a second image which includes the correct-answer graphic symbol and a plurality of graphic symbols P21 to P23 similar to the correct-answer graphic symbol; display 10 displays the first image to cause the subject to memorize the correct-answer graphic symbol, and displays the second image to evaluate memory recall of the subject immediately after the display of the first image is ended; the case characteristic data indicates a characteristic that cognitive function is lower as a percentage of viewpoints of the subject present in a display area of the correct-answer graphic symbol in the second image is smaller; and diagnostic unit 39 calculates the percentage of the viewpoints present in the display area of the correct-answer graphic symbol in the distribution map, and diagnoses that there is a possibility of a decrease in cognitive function when the calculated percentage is smaller than or equal to a threshold value.

In this way, the second diagnostic process makes it possible to diagnose a decrease in cognitive function in a simple and easy way. Furthermore, the second diagnostic process can be executed in short time of several tens of seconds, and thus can achieve convenience, low cost, objectivity, quantitativity, and versatility (language independence).

Here, diagnostic unit 39 may further normalize the percentage of the viewpoints present in the display area of the correct-answer graphic symbol to transform the percentage into a score.

In this way, it is possible to quantify the degree of the decrease in cognitive function. The second diagnostic process makes it possible to obtain diagnostic results similar to those obtainable by the conventional MMSE, and further makes it possible to detect patients with early-stage dementia who cannot be detected by the conventional MMSE.

It is to be noted that, in FIG. 8, Step S28 may be executed between Step S25 and S26, and a threshold value in Step S26 may be a predetermined score (for example, score 2 on the scale of 5). In other words, PC 30 may normalize the calculated percentage to transform the percentage to a score after Step S25 in FIG. 8, and then may diagnose that there is a possibility of a decrease in cognitive function when the score is smaller than or equal to the threshold value.

In addition, the above-described correct-answer graphic symbol is not limited to a graphic symbol, and may be a character or an image, or may be an any combination of a graphic symbol, a character, an image, etc. Likewise, each of the similar graphic symbols is not limited to a graphic symbol, and may be a character or an image, or may be an any combination of a graphic symbol, a character, an image, etc.

[1.2.3 Third Diagnostic Process]

Next, the third diagnostic process is described in detail. The third diagnostic process uses the above-described third characteristic. In other words, the third diagnostic process uses a characteristic that a patient with corticobasal degeneration neglects a unilateral space.

Figure 9:
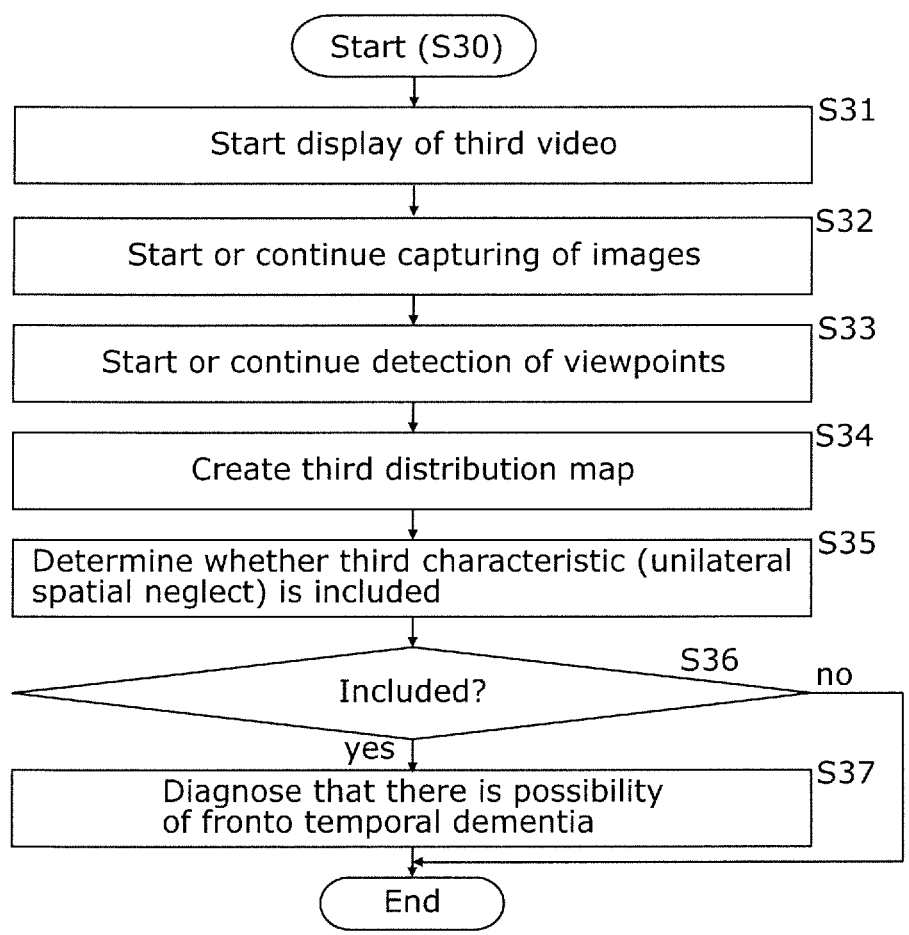
FIG. 9 is a flow chart indicating one example of a third diagnostic process in FIG. 5.

FIG. 9 is a flow chart indicating one example of a third diagnostic process (S30) in FIG. 5. As illustrated in FIG. 9, first, PC 30 reads out third video data 303 from storage unit 32, and starts to display a third video indicated by third video data 303 in display 10 (S31).

Figure 15A:
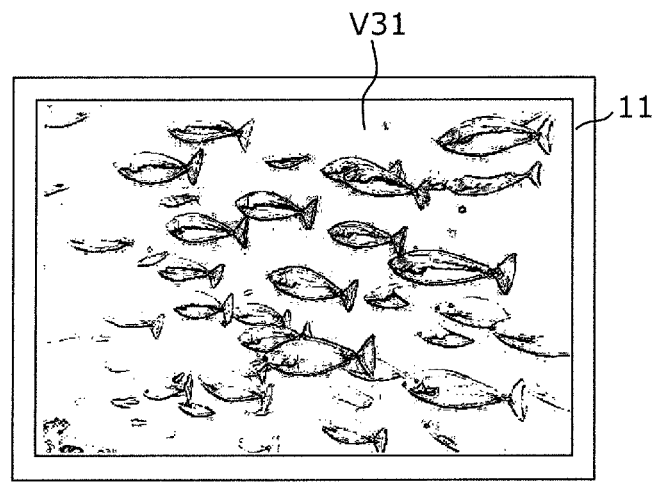
FIG. 15A is a diagram illustrating a first example of a third video according to the embodiment.
Figure 15B:
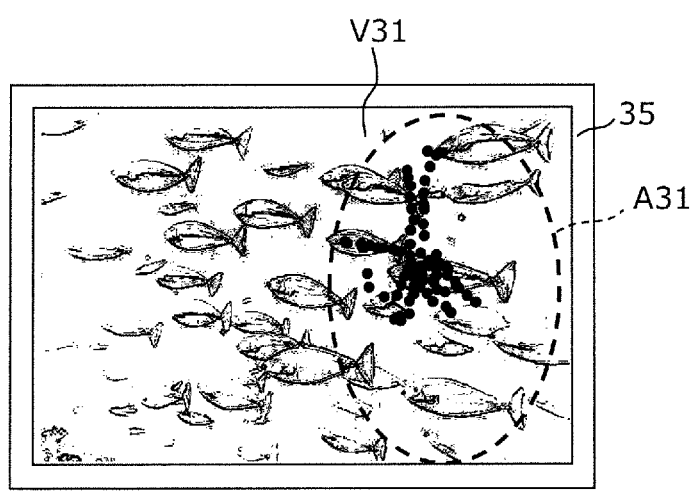
FIG. 15B is a diagram illustrating a display example obtained by superimposing a third distribution map of a patient with corticobasal degeneration on the third video in FIG. 15A.
Figure 15C:
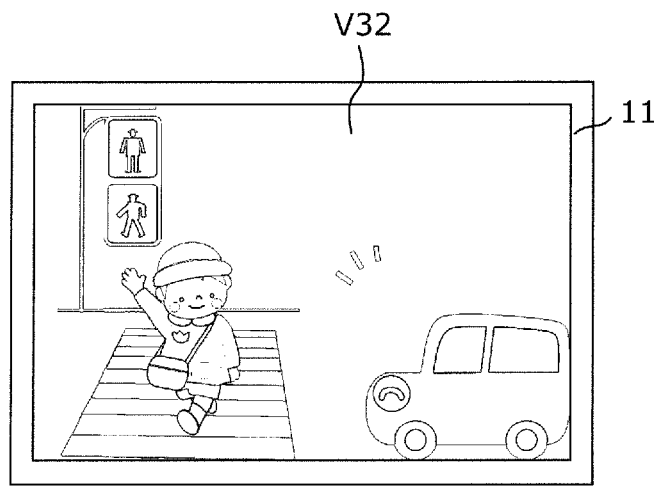
FIG. 15C is a diagram illustrating a second example of a third video according to the embodiment.
Figure 15D:
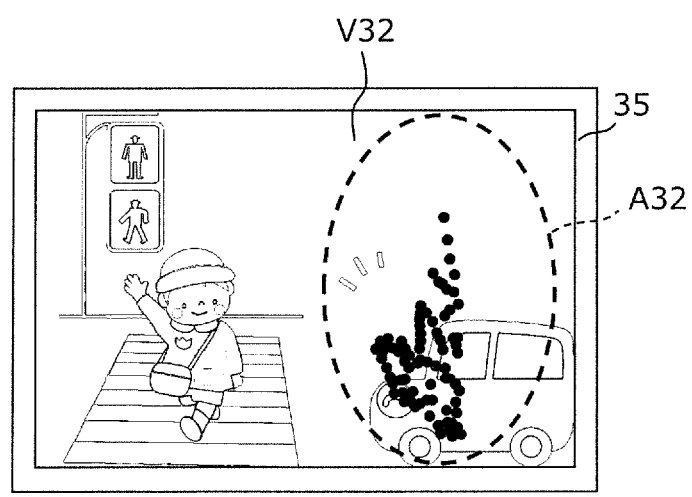
FIG. 15D is a diagram illustrating a display example obtained by superimposing a third distribution map of a patient with corticobasal degeneration on the third video in FIG. 15C.
Figure 15E:
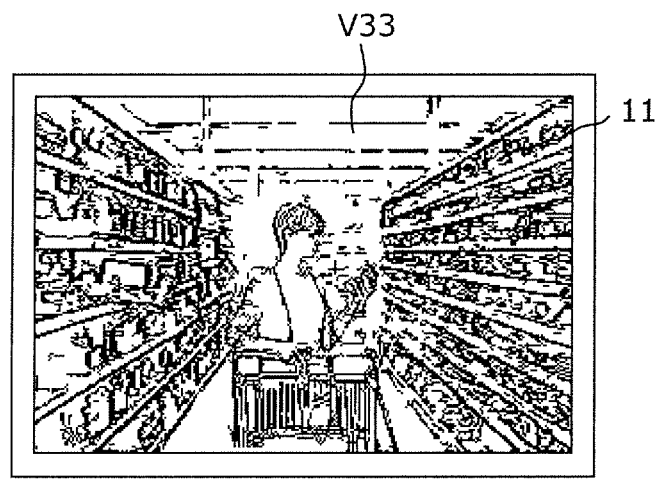
FIG. 15E is a diagram illustrating a third example of a third video according to the embodiment.

FIG. 15A, FIG. 15C, and FIG. 15E are diagrams illustrating a first example, a second example, and a third example of a third video in the embodiment, respectively.

In FIG. 15A, image V31 of a fish group is displayed on display surface 11 as a third video. In FIG. 15C, image V32 of a crosswalk, a traffic signal, a child, and a car is displayed on display surface 11 as a third video. In FIG. 15E, image V33 of shelves in a supermarket and a customer is displayed on display surface 11 as a third video. Although image V31 to image V33 are represented as line drawings for convenience, image V31 to image V33 may be actually full-colour images.

PC 30 may display one of image V31 to image V33, or may display two or more of image V31 to image V33 while sequentially switching the two or more of image V31 to image V33 during a period of the third diagnostic process (during a period from time points t2 to t3 in FIG. 6).

PC 30 further causes imaging unit 21 to start to capture images of eyes of a subject or to continue performing ongoing image capturing (S32), and to start to detect viewpoints of the subject or to continue performing ongoing viewpoint detection (S33). Furthermore, PC 30 obtains viewpoint data from detection unit 37 from start to end of display of the third video, and creates a third distribution map corresponding to the third video in real time (S34), displays the third video in display unit 35, and superimposes the third distribution map on the third video in display unit 35. The following processes are executed in parallel: display of the third video in display 10 and display unit 35; image capturing by imaging unit 21; viewpoint detection by PC 30 (specifically, detection unit 37 in FIG. 1); and creation of the third distribution map by PC 30 (specifically, creation unit 38 in FIG. 1).

Subsequently, PC 30 determines whether the third distribution map includes a third characteristic in case characteristic data (S35), and when the answer is positive (yes in S36), it is diagnosed that there is a possibility of corticobasal degeneration (S37). The third characteristic indicates a characteristic of unilateral spatial neglect which is a characteristic that no viewpoint is present in the left half of an image.

Figure 15F:
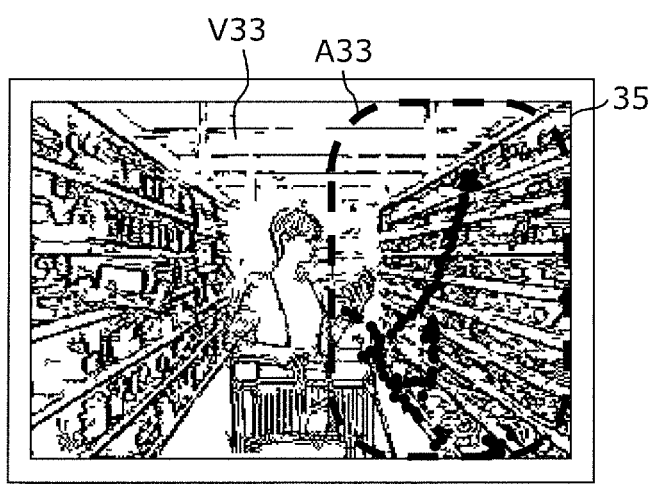
FIG. 15F is a diagram illustrating a display example obtained by superimposing a third distribution map of a patient with corticobasal degeneration on the third video in FIG. 15E.

FIG. 15B, FIG. 15D, and FIG. 15F are diagrams illustrating examples in which the third distribution map is superimposed on the respective videos in FIG. 15A, FIG. 15C, and FIG. 15E. In FIG. 15B, FIG. 15D, and FIG. 15F, the third distribution map of a patient with corticobasal degeneration is superimposed. In each of the diagrams, no viewpoint is present in the left half of each of the images although viewpoints are present in the corresponding one of broken-line frames A31, A32, and A33 in the right half of the images. In other words, the third distribution map superimposed on each diagram includes a third characteristic (that is, a characteristic of unilateral spatial neglect).

In the example of each of FIG. 15B, FIG. 15D, and FIG. 15F, PC 30 is to determine that the third distribution map includes the third characteristic in Step S35, and to diagnose that there is a possibility of corticobasal degeneration in Step S37.

As described above, in the third diagnostic process: the video for diagnosis includes a still image of at least one of a person, an object, a landscape, or a graphic symbol; the case characteristic data indicates a characteristic that a left-side space is neglected, and that the characteristic corresponds to corticobasal degeneration included in cognitive impairment; and diagnostic unit 39 diagnoses that there is a possibility of corticobasal degeneration included in cognitive impairment when the distribution map has the characteristic.

In this way, the third diagnostic process makes it possible to discriminate corticobasal degeneration from the other cases in cognitive impairment in a simple and easy way. Furthermore, the third diagnostic process can be executed in short time of several tens of seconds, and thus can achieve convenience, low cost, objectivity, quantitativity, and versatility (language independence).

[1.2.4 Fourth Diagnostic Process]

Next, the fourth diagnostic process is described in detail. The fourth diagnostic process uses the above-described fourth characteristic. In other words, the fourth diagnostic process uses a characteristic that viewpoints of a patient with dementia with Lewy bodies are gathered in an inducing image which induces visual hallucination of a human face.

Figure 10:
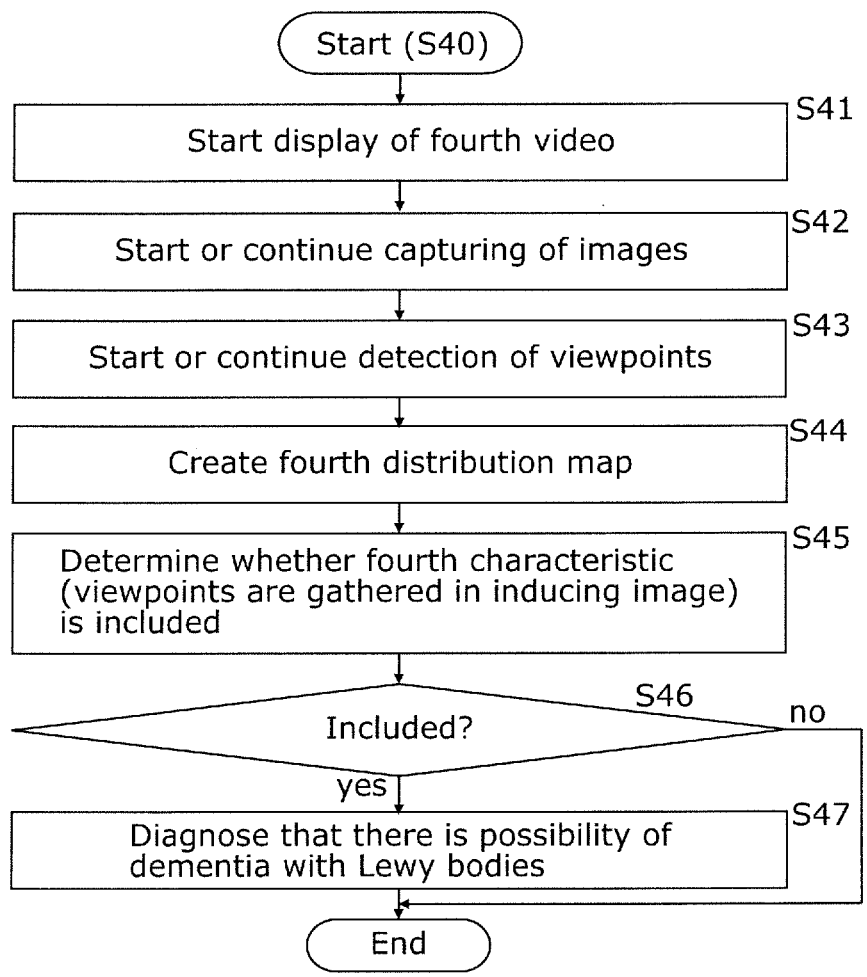
FIG. 10 is a flow chart indicating one example of a fourth diagnostic process in FIG. 5.

FIG. 10 is a flow chart indicating one example of a fourth diagnostic process (S40) in FIG. 5. As illustrated in FIG. 10, PC 30 reads out fourth video data 304 from storage unit 32, and starts to display a fourth video indicated by fourth video data 304 in display 10 (S41).

Figure 16A:
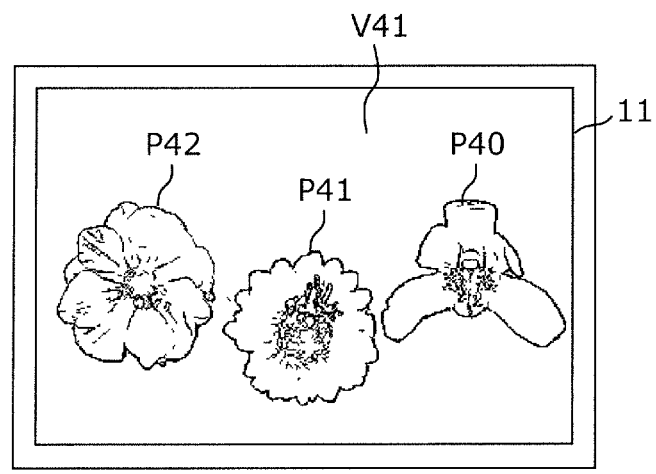
FIG. 16A is a diagram illustrating an example of a fourth video according to the embodiment.

FIG. 16A is a diagram illustrating an example of a fourth video according to the embodiment. In FIG. 16A, image V41 is displayed on display surface 11 as a fourth video. Still image V41 includes inducing image P40 which induces visual hallucination of a human face and a plurality of non-inducing images P41 and P42 which do not induce visual hallucination. Each of inducing image P40 and non-inducing images P41 and P42 is an image of flowers. Although the fourth video is a line drawing in FIG. 16A, it is to be noted that the fourth video may be a full-colour video.

PC 30 may display single still image V41, or display a plurality of still images including the inducing image and the plurality of non-inducing images while sequentially switching the plurality of still images during a period of the fourth diagnostic process (during a period from time points t3 to t4 in FIG. 6). It is to be noted that the fourth video may include a message image which prompts gaze such as "Please gaze an attracting thing." In addition, PC 30 may repeatedly output, to a subject, a message voice which prompts gaze such as "Please gaze an attracting thing." while the fourth video is being displayed. Furthermore, PC 30 may use both the message image and the message voice.

PC 30 further causes imaging unit 21 to start to capture images of eyes of the subject or to continue performing ongoing image capturing (S42), and to start to detect viewpoints of the subject or to continue performing ongoing viewpoint detection (S43). Furthermore, PC 30 obtains viewpoint data from detection unit 37 from start to end of display of the fourth video, and creates a fourth distribution map corresponding to the fourth video in real time (S44), displays the fourth video in display unit 35, and superimposes the fourth distribution map on the fourth video in display unit 35. The following processes are executed in parallel: display of the fourth video in display 10 and display unit 35; image capturing by imaging unit 21; viewpoint detection by PC 30 (specifically, detection unit 37 in FIG. 1); and creation of the fourth map by PC 30 (specifically, creation unit 38 in FIG. 1).

Subsequently, PC 30 determines whether the fourth distribution map includes a fourth characteristic in case characteristic data (S45), and when the answer is positive (yes in S46), it is diagnosed that there is a possibility of dementia with Lewy bodies (S47).

Figure 16B:
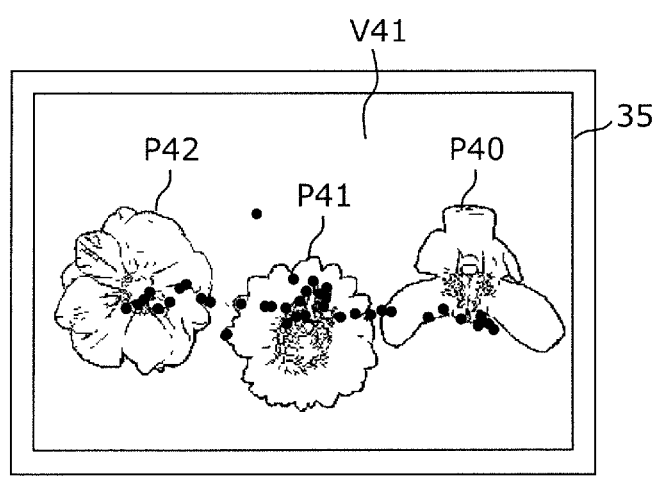
FIG. 16B is a diagram illustrating a display example obtained by superimposing a fourth distribution map of a patient with Alzheimer's disease on the fourth video in FIG. 16A.

FIG. 16B is a diagram illustrating a display example obtained by superimposing a fourth distribution map of a patient with Alzheimer's disease on the fourth video in FIG. 16A. In addition, FIG. 16C is a diagram illustrating a display example obtained by superimposing a fourth distribution map of a patient with dementia with Lewy bodies on the fourth video in FIG. 16A.

In a fourth distribution map in FIG. 16B, viewpoints are present almost evenly in inducing image P40, and non-inducing images P41 and P42. Meanwhile, in a fourth distribution map in FIG. 16C, viewpoints are gathered in inducing image P40, and no viewpoint is present in non-inducing images P41 and P42. In other words, the fourth distribution map in FIG. 16B does not include the fourth characteristic, but the fourth distribution map in FIG. 16C includes the fourth characteristic.

In the example in FIG. 16B, PC 30 determines that the fourth distribution map does not include the fourth characteristic in Step S45, and thus PC 30 does not diagnose that there is a possibility of dementia with Lewy bodies.

Figure 16C:
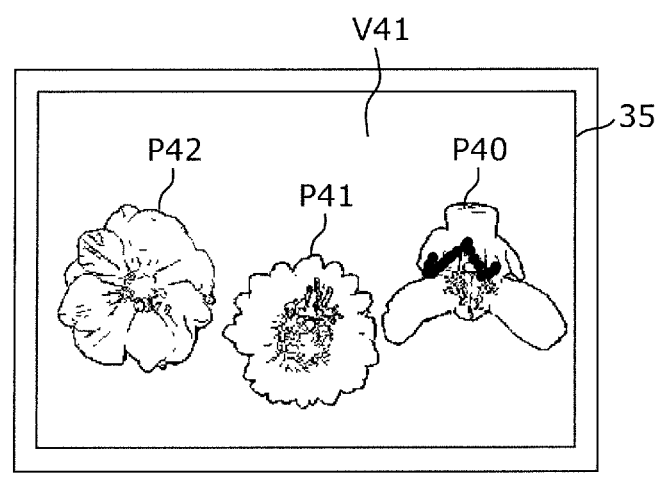
FIG. 16C is a diagram illustrating a display example obtained by superimposing a fourth distribution map of a patient with dementia with Lewy bodies on the fourth video in FIG. 16A.

In the example in FIG. 16C, PC 30 determines that the fourth distribution map includes the fourth characteristic in Step S45, and thus PC 30 diagnoses that there is a possibility of dementia with Lewy bodies in Step 47.

As described above, in the fourth diagnostic process: the video for diagnosis includes a still image including an inducing image which induces visual hallucination and a plurality of non-inducing images which do not induce visual hallucination; the case characteristic data indicates that viewpoints are gathered in the inducing image; and diagnostic unit 39 diagnoses that there is a possibility of dementia with Lewy bodies included in cognitive impairment when the viewpoints are gathered in the inducing image in the distribution map.

In this way, the fourth diagnostic process makes it possible to discriminate dementia with Lewy bodies from the other cases in cognitive impairment in a simple and easy way. Furthermore, the fourth diagnostic process can be executed in short time of several tens of seconds, and thus can achieve convenience, low cost, objectivity, quantitativity, and versatility (language independence).

[1.2.5 Fifth Diagnostic Process]

Next, the fifth diagnostic process is described in detail. The fifth diagnostic process uses the above-described fifth characteristic. In other words, the fifth diagnostic process uses a characteristic that it is difficult for the eyes of a patient with a decrease in cognitive function to track a moving object in a video.

Figure 11:
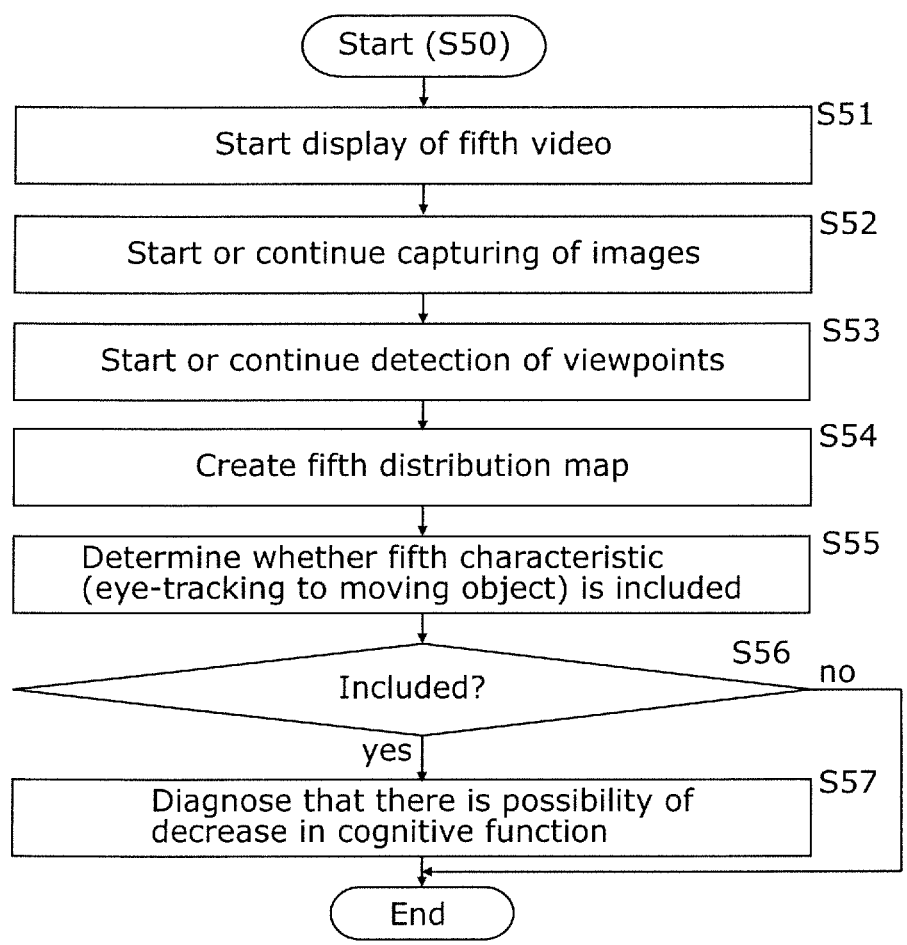
FIG. 11 is a flow chart indicating one example of a fifth diagnostic process in FIG. 5.

FIG. 11 is a flow chart indicating one example of a fifth diagnostic process (S50) in FIG. 5. As illustrated in FIG. 11, PC 30 reads out fifth video data 305 from storage unit 32, and starts to display a fifth video indicated by fifth video data 305 in display 10 (S51).

Figure 17:
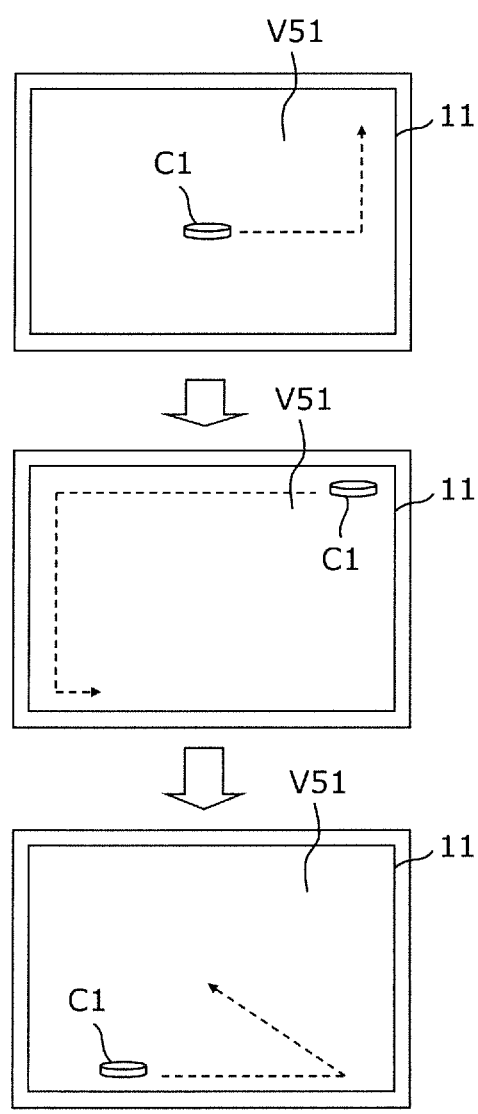
FIG. 17 is a diagram illustrating an example of a fifth video according to the embodiment.

FIG. 17 is a diagram illustrating an example of a fifth video according to the embodiment. In the upper, middle, and lower rows in FIG. 17, video V51 of an object (coin C1 in the diagram) that moves as time passes is displayed on display surface 11 as a fifth video. The image of coin C1 in the diagram moves vertically and horizontally on display surface 11 as indicated by the broken lines in the diagrams. Although the fifth video is a line drawing in FIG. 17, it is to be noted that the fifth video may be a full-colour video.

PC 30 may display single video V51, or display a plurality of videos of a moving object while sequentially switching the plurality of videos of the moving object during a period of the fifth diagnostic process (during a period from time points t4 to t5 in FIG. 6). It is to be noted that the fifth video may include a message image which prompts gaze such as "Please gaze a coin." In addition, PC 30 may repeatedly output, to a subject, a message voice which prompts gaze such as "Please gaze a coin." while the fifth video is being displayed. Furthermore, PC 30 may use both the message image and the message voice.

PC 30 further causes imaging unit 21 to start to capture images of eyes of a subject or to continue performing ongoing image capturing (S52), and to start to detect viewpoints of the subject or to continue performing ongoing viewpoint detection (S53). Furthermore, PC 30 obtains viewpoint data from detection unit 37 from start to end of display of the fifth video, and creates a fifth distribution map corresponding to the fifth video in real time (S54), displays the fifth video in display unit 35, and superimposes the fifth distribution map on the fifth video in display unit 35. The following processes are executed in parallel: display of the fifth video in display 10 and display unit 35; image capturing by imaging unit 21; viewpoint detection by PC 30 (specifically, detection unit 37 in FIG. 1); and creation of the fifth map by PC 30 (specifically, creation unit 38 in FIG. 1).

Subsequently, PC 30 determines whether the fifth distribution map includes a fifth characteristic in case characteristic data (S55), and when the answer is positive (yes in S56), it is diagnosed that there is a possibility of a decrease in cognitive function (S57).

As described above, in the fifth diagnostic process: the video for diagnosis includes a video (V51) of a moving object on the display surface; the case characteristic data indicates that a viewpoint of the subject is unable to track the moving object; and diagnostic unit 39 diagnoses that there is a possibility of a decrease in cognitive function when the viewpoint has not tracked the moving object in the distribution map.

In this way, the fifth diagnostic process makes it possible to diagnose a decrease in cognitive function in a simple and easy way. Furthermore, the fifth diagnostic process can be executed in short time of several tens of seconds, and thus can achieve convenience, low cost, objectivity, quantitativity, and versatility (language independence).

[1.2.6 Sixth Diagnostic Process]

Next, the sixth diagnostic process is described in detail. The sixth diagnostic process uses the above-described sixth characteristic. In other words, the sixth diagnostic process uses a characteristic that a viewpoint obtainment percentage of a patient with fronto-temporal dementia is lower than those of patients of the other cases of dementia. The viewpoint obtainment percentage is a percentage of time during which view points are present on display surface 11. A viewpoint obtainment percentage becomes smaller with increase in time during which viewpoints are present outside of display surface 11.

Figure 12:
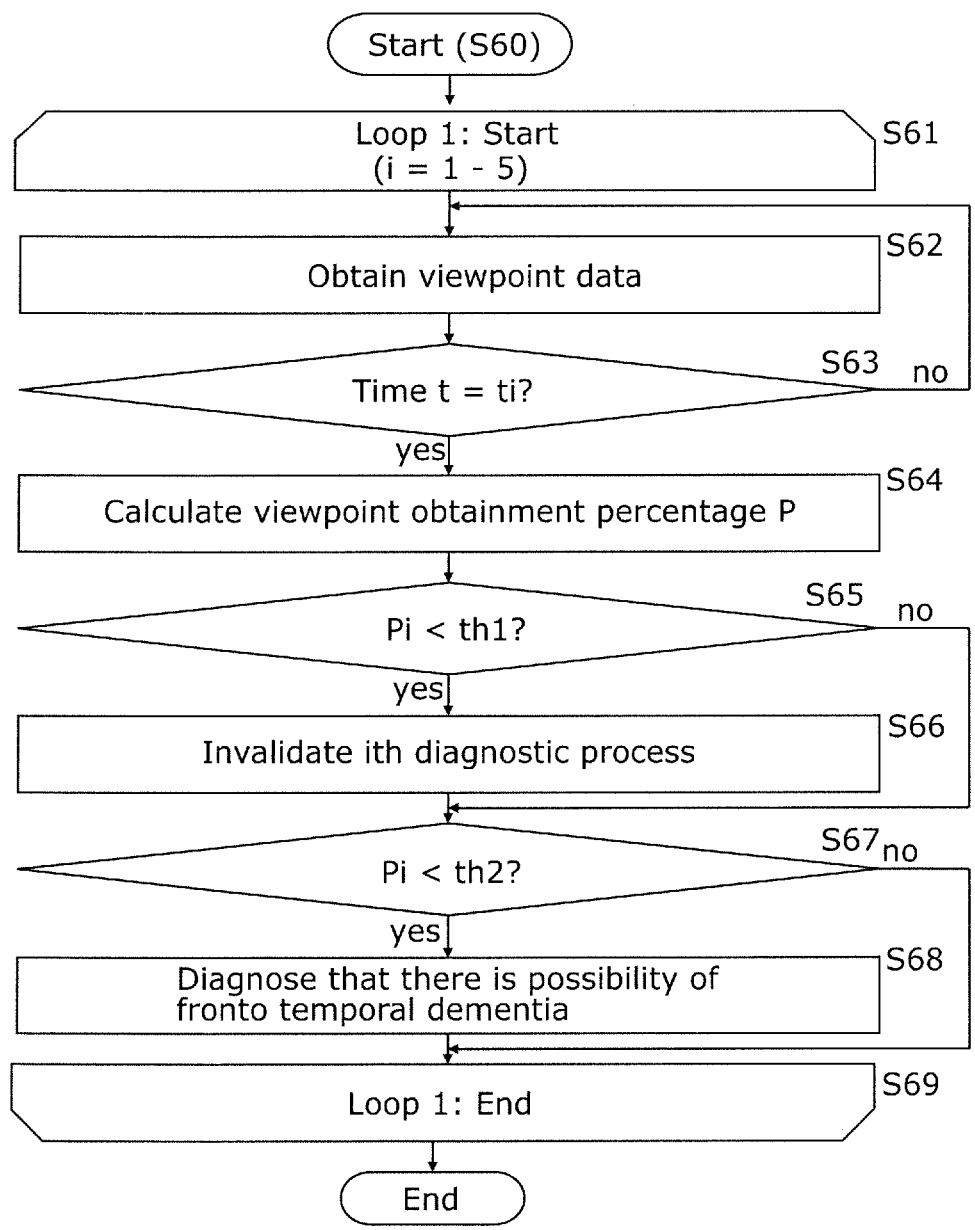
FIG. 12 is a flow chart indicating one example of a sixth diagnostic process in FIG. 6.

FIG. 12 is a flow chart indicating one example of a sixth diagnostic process (S60) in FIG. 6. As in the example illustrated in FIG. 6, the sixth diagnostic process in the diagram is executed in parallel with the first diagnostic process to the fifth diagnostic process. Loop 1 (S61 to S69) has five iterations each performed in synchronization with a corresponding one of the first diagnostic process to the fifth diagnostic process.

In the case of i=1 (that is, a first iteration), a first video is displayed in display 10. PC 30 obtains viewpoint data from detection unit 37 in a period during which the first video is displayed (a period from time point t=0 to t=t1 in FIG. 6) (S62, S63). PC 30 calculates viewpoint obtainment percentage P1 in the period during which the first video is displayed, at the time when the display of the first video is ended (time point t1 in FIG. 6). When calculated viewpoint obtainment percentage P1 is smaller than first threshold value th1 (yes in S65), PC 30 invalidates the first diagnostic process (S66). When calculated viewpoint obtainment percentage P1 is smaller than second threshold value th2 (yes in S67), PC 30 diagnoses that there is a possibility of fronto-temporal dementia (S68). Here, first threshold value th1 is an indicator indicating whether the first diagnostic process satisfies a precondition for valid first diagnostic process. In other words, in the diagnostic process for cognitive impairment by viewpoint detection, it is a precondition that a patient is looking at a video for diagnosis displayed for the subject. First threshold value th1 may be, for example, 0.8 when viewpoint obtainment percentage P1 is in a range from 0 to 1. In addition, second threshold value th2 is an indicator for determining whether the sixth characteristic is present. Second threshold value th2 may be, for example, 0.8 when viewpoint obtainment percentage P1 is in a range from 0 to 1. In addition, first threshold value th1 and second threshold value th2 may be the same value, or may be different values.

The cases of i=2-5 (that is, second to fifth iterations) are almost the same as the case of i=1 (that is, first iteration).

It is to be noted that results of the five iterations in Step S65 in FIG. 12 are not always the same, but the results of the five iterations are displayed in display unit 35 as they are. Likewise, it is to be noted that results of the five iterations in Step S67 in FIG. 12 are not always the same, but the results of the five iterations are displayed in display unit 35 as they are.

Although FIG. 12 illustrates the example of the loop processing with the five iterations as the sixth diagnostic process, examples are not limited thereto. For example, the sixth diagnostic process may be a process corresponding to a single iteration (that is, S62 to S68 in FIG. 12) throughout the period for the first diagnostic process to the fifth diagnostic process (the period from t=0 to t=5 in FIG. 6). In addition, as another example, the sixth diagnostic process may be a process corresponding to a single iteration (that is, S62 to S68 in FIG. 12) only in the period for any one of the first diagnostic process to the fifth diagnostic process.

Furthermore, the sixth diagnostic process can be executed not in parallel but independently. For example, the first to fifth videos or another video may be displayed as a sixth video, and S64 to S68 in FIG. 12 may be executed.

Next, data related to viewpoint obtainment percentages which are of a plurality of subjects and are collected by the Inventors of the present application is introduced.

Figure 19:
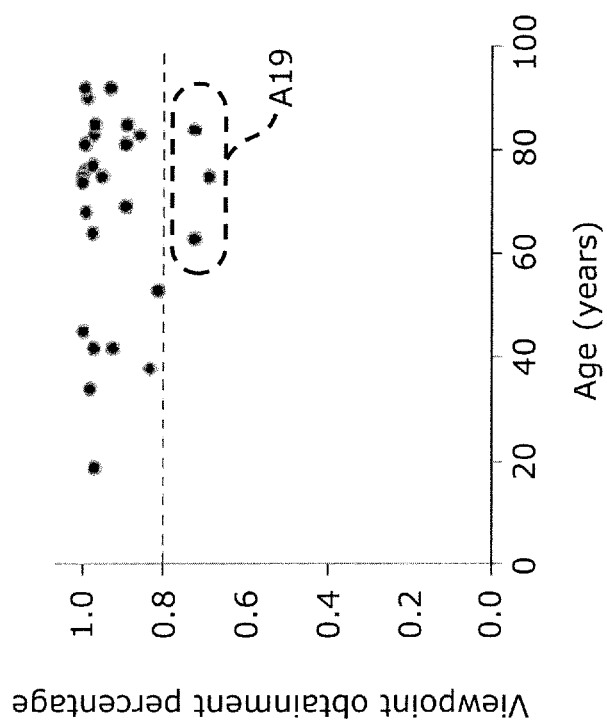
FIG. 19 is a diagram indicating viewpoint obtainment percentages on the basis of the ages of subjects.

FIG. 19 is a diagram indicating viewpoint obtainment percentages on the basis of the ages of subjects. The horizontal axis in the diagram indicates the ages of the subjects. The vertical axis indicates the viewpoint obtainment percentages of approximately 30 subjects in diagnostic processes. In the diagram, high viewpoint obtainment percentages of 0.8 or above are obtained from the subjects except for three subjects indicated in broken-line frame A19. In other words, it is demonstrated that even a very elderly subject aged 90 or above can get a high viewpoint obtainment percentage irrespective of the age.

Figure 20:
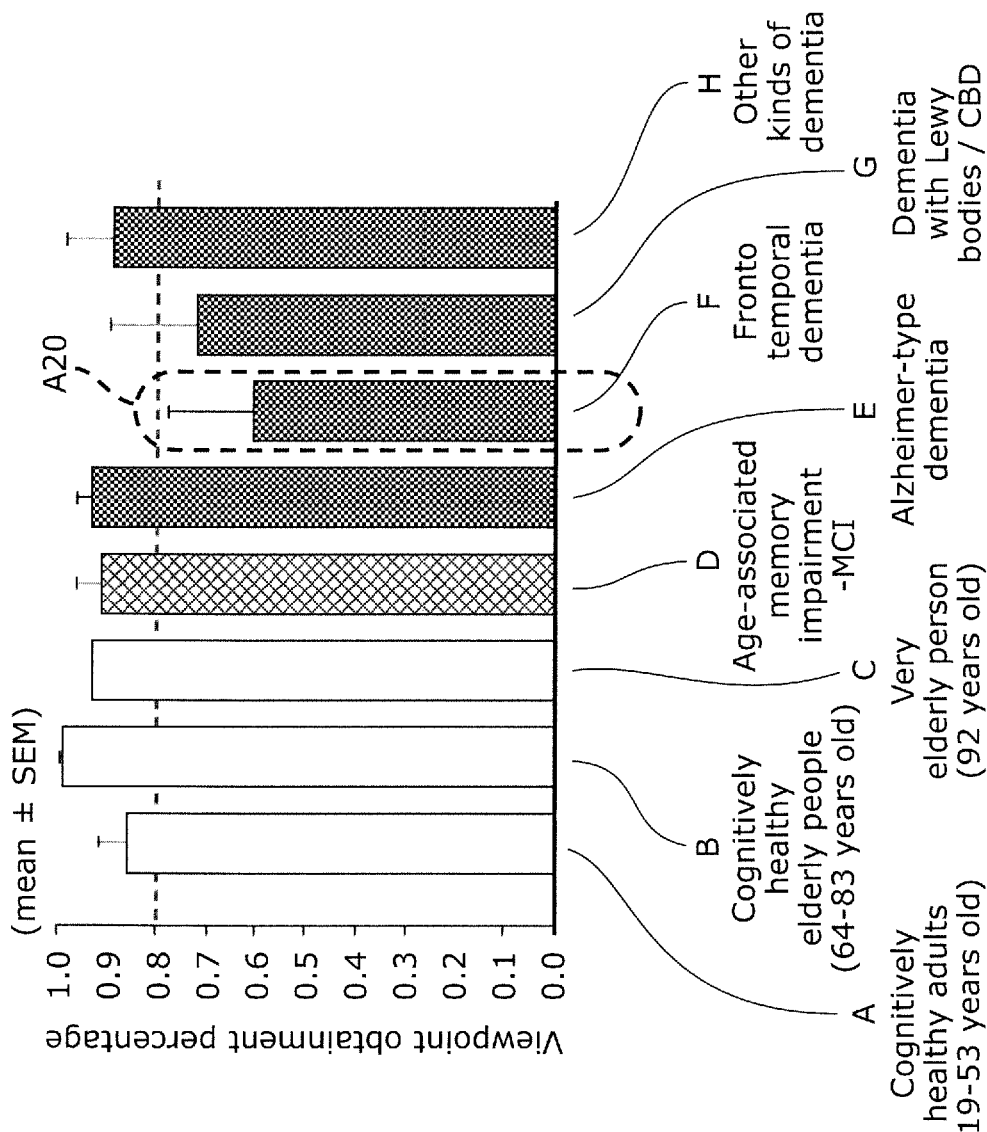
FIG. 20 is a diagram indicating viewpoint obtainment percentages on the basis of the cases of subjects.

FIG. 20 is a diagram indicating viewpoint obtainment percentages on the basis of the cases of the subjects. In FIG. 20, the horizontal axis indicates the categories of cases of the subjects who are the same as in FIG. 19. The vertical axis indicates viewpoint obtainment percentages. Each of bars in the graph indicates a mean and a standard error of mean (SEM).

As indicated by the horizontal axis, the subjects are categorized under cases A to H. A indicates a plurality of subjects who are cognitively healthy adults aged 19 to 53. B indicates a plurality of subjects who are cognitively healthy elderly people aged 64 to 83. C indicates a subject who is a very elderly person aged 92. D indicates a plurality of subjects with age-associated memory impairment or with mild cognitive impairment (MCI). E indicates a plurality of subjects with Alzheimer's disease. F indicates a plurality of subjects with fronto-temporal dementia. G indicates a plurality of subjects with dementia with Lewy bodies. H indicates subjects with another kind of dementia.

In the diagram, high viewpoint obtainment percentages are obtained except for F (fronto-temporal dementia) indicated with broken-line frame A20. The subjects with fronto-temporal dementia of F indicated with broken-line frame A20 are the same as the three subjects indicated by broken-line circle A19 in FIG. 19. In view of this, it is known that subjects with fronto-temporal dementia get a mean viewpoint obtainment percentage lower than (smaller by 0.8 in FIG. 20 than) those in the other cases even after a standard error of mean is added to the mean viewpoint obtainment percentage. This indicates that there is a significant difference. In other words, FIG. 20 supports the six characteristic which has been explained already. In the data example in FIG. 20, it is known that 0.8 is excellent as the above second threshold value.

It is to be noted that the viewpoint obtainment percentage is considered to be affected by environmental conditions such as the size of display surface 11 and the distance between display surface 11 and each subject. First threshold value th1 and second threshold value th2 do not always need to be 0.8, and may be determined according to environmental conditions.

As described above, in the sixth diagnostic process, diagnostic unit 39 calculates a viewpoint obtainment percentage indicating a percentage of viewpoints present on the display surface in the distribution map, and diagnoses that there is a possibility of fronto-temporal dementia included in cognitive impairment when the viewpoint obtainment percentage is smaller than or equal to a predetermined value.

In this way, the sixth diagnostic process makes it possible to diagnose fronto-temporal dementia in a simple and easy way. Furthermore, the sixth diagnostic process can be executed in short time of several tens of seconds, and thus can achieve convenience, low cost, objectivity, quantitativity, and versatility (language independence).

As described above, cognitive impairment diagnostic apparatus 1 according to an aspect of this embodiment includes: display 10 which displays a video for diagnosis of cognitive impairment on display surface 11; imaging unit 21 which captures images of an eye of a subject; detection unit 37 which detects viewpoints of the subject on display surface 11 in time series based on the images captured by imaging unit 21; creation unit 38 which creates a distribution map representing a distribution of the viewpoints detected by detection unit 37; storage unit 32 which stores case characteristic data 310 indicating a characteristic of a viewpoint distribution corresponding to a typical case in cognitive impairment; and diagnostic unit 39 which diagnoses cognitive impairment of the subject by determining whether the distribution map has the characteristic indicated by the case characteristic data.

With this configuration, in diagnosis of cognitive impairment by cognitive impairment diagnostic apparatus 1, it is possible to achieve convenience, low cost, objectivity, quantitativity, and versatility (language independence).

Here, the video for diagnosis may include a first video to a fifth video. The first video may include an image of at least one of a person, an object, a landscape, or a graphic symbol. The second video may be a video including: a first image which includes a correct-answer graphic symbol and does not include any graphic symbol other than the correct-answer graphic symbol; and a second image which includes the correct-answer graphic symbol and a plurality of graphic symbols similar to the correct-answer graphic symbol. The third video may include a still image of at least one of a person, an object, a landscape, or a graphic symbol. The fourth video may include: a still image including an inducing graphic symbol which induces visual hallucination; and a plurality of non-inducing graphic symbols which do not induce visual hallucination. The fifth video may include a video of a moving object on the display surface. Display 10 may display each of the first video to the fifth video in a display period ranging from 10 seconds to 30 seconds inclusive. Diagnostic unit 39 may diagnose whether there is a possibility of each of decreases in cognitive function, fronto-temporal dementia, corticobasal degeneration, and dementia with Lewy bodies, based on a distribution map corresponding to the display period of each of the first video to the fifth video.

With this configuration, in the diagnosis using the first video to the fifth video, it is possible to diagnose whether there is a decrease in cognitive function and the degree of the decrease, and furthermore to discriminate a case when a decrease in cognitive function is seen from the other cases, in a short period of several minutes. For example, it is possible to achieve significant reduction in time necessary for medical examinations and increase in efficiency of mass health screening, and thus to cope with explosive increase in the population of elderly people.

Here, diagnostic unit 39 may further calculate a viewpoint obtainment percentage indicating a percentage of viewpoints present on display surface 11 on the distribution map corresponding to each of the first video to the fifth video, invalidate a corresponding diagnostic result when the viewpoint obtainment percentage is smaller than or equal to a predetermined value, and diagnose that there is a possibility of fronto-temporal dementia included in cognitive impairment.

In this way, based on viewpoint obtainment percentages, it is possible to determine the validity of each of the diagnoses made by cognitive impairment diagnostic apparatus 1, and to discriminate fronto-temporal dementia from the other cases.

In addition, a cognitive impairment diagnostic program according to an aspect of this embodiment is for use in a computer which is connected to imaging unit 21 and display 10 including display surface 11 and includes storage unit 32 which stores case characteristic data 310 indicating characteristics of viewpoint distributions corresponding respectively to typical cases in cognitive impairment. The program causes the computer to execute: displaying a video for diagnosis of cognitive impairment on a display surface; capturing images of an eye of a subject by imaging unit 21; detecting viewpoints of the subject on display surface 11 in time series based on the images captured by imaging unit 21; creating a distribution map representing a distribution of the viewpoints detected; and diagnosing cognitive impairment of the subject by determining whether the distribution map has the characteristic indicated by the case characteristic data.

It is to be noted that cognitive impairment diagnostic apparatus 1 may be used for a plurality of targets at the same time. In this case, it is excellent that imaging unit 21 captures images of the plurality of subjects, detection unit 37 detects viewpoints of each subject, creation unit 38 creates a distribution map of the subject, and diagnostic unit 39 makes a diagnosis for the subject. In addition, cognitive impairment diagnostic apparatus 1 may include a plurality of imaging devices 20 when a plurality of subjects are targets at the same time. In this case, single imaging device 20 is used for a single subject or a plurality of subjects. In this way, cognitive impairment diagnostic apparatus 1 is capable of increasing the efficiency in mass health screening.

The embodiment and variations thereof are described as examples for the purpose of explaining the technical details of the present invention, and thus are not intended to limit the technical scope of the invention according to the present application to the details described herein. The technical scope of the invention according to the present application encompasses embodiments that a person skilled in the art may arrive at by performing modification, replacement, addition, and omission onto the examples within the scope of the DESCRIPTION, the Drawings, and the CLAIMS, and the scope of equivalents thereof.

INDUSTRIAL APPLICABILITY

The present invention relates to a cognitive impairment diagnostic apparatus and a cognitive impairment diagnostic program for diagnosing cognitive impairment.

REFERENCE SIGNS LIST 1 cognitive impairment diagnostic apparatus
10 display
11 display surface
20 imaging device
21 imaging unit
22, 23 camera
24 light source unit
25, 26 light source
30 PC
31 processor
32 storage unit
33 input unit
34 output unit
35 display unit
36 interface unit
37 detection unit
38 creation unit
39 diagnostic unit
300 video data for diagnosis
301 first video data
302 second video data
303 third video data
304 fourth video data
305 fifth video data
310 case characteristic data
311 first characteristic data
312 second characteristic data 313 third characteristic data
314 fourth characteristic data
315 fifth characteristic data
320 program
321 cognitive impairment diagnostic program
322 viewpoint data
323 distribution map data

The invention claimed is:

1. A cognitive impairment diagnostic apparatus, comprising:
a display which displays a video for diagnosis of cognitive impairment on a display surface;
an imaging unit configured to capture images of an eye of a subject;
a detection unit configured to detect viewpoints of the subject on the display surface in time series based on the images captured by the imaging unit;
a creation unit configured to create a distribution map representing a distribution of the viewpoints detected by the detection unit;
a storage unit configured to store case characteristic data indicating a characteristic of a viewpoint distribution corresponding to a typical case in cognitive impairment; and
a diagnostic unit configured to diagnose cognitive impairment of the subject by determining whether the distribution map has the characteristic indicated by the case characteristic data.

2. The cognitive impairment diagnostic apparatus according to claim 1,
wherein the video for diagnosis includes an image of at least one of a person, an object, a landscape, or a graphic symbol,
the case characteristic data indicates a one-point gaze pattern in which viewpoints are continuously gathered in a local part having one point as a center, and
the diagnostic unit is configured to diagnose that there is a possibility of fronto-temporal dementia included in cognitive impairment when the distribution map has the characteristic.

3. The cognitive impairment diagnostic apparatus according to claim 1,
wherein the video for diagnosis is a video including: a first image which includes a correct-answer graphic symbol and does not include any graphic symbol other than the correct-answer graphic symbol; and a second image which includes the correct-answer graphic symbol and a plurality of graphic symbols similar to the correct-answer graphic symbol,
the display which displays the first image to cause the subject to memorize the correct-answer graphic symbol, and display the second image to evaluate memory recall of the subject immediately after the display of the first image is ended,
the case characteristic data indicates a characteristic that cognitive function is lower as a percentage of viewpoints of the subject present in a display area of the correct-answer graphic symbol in the second image is smaller, and
the diagnostic unit is configured to calculate the percentage of the viewpoints present in the display area of the correct-answer graphic symbol in the distribution map, and diagnose that there is a possibility of a decrease in cognitive function when the calculated percentage is smaller than or equal to a threshold value.

4. The cognitive impairment diagnostic apparatus according to claim 3,
wherein the diagnostic unit is further configured to normalize the percentage of the viewpoints present in the display area of the correct-answer graphic symbol to transform the percentage into a score.

5. The cognitive impairment diagnostic apparatus according to claim 1,
wherein the video for diagnosis includes a still image of at least one of a person, an object, a landscape, or a graphic symbol,
the case characteristic data indicates a characteristic that a left-side space is neglected, and that the characteristic corresponds to corticobasal degeneration included in cognitive impairment, and
the diagnostic unit is configured to diagnose that there is a possibility of corticobasal degeneration included in cognitive impairment when the distribution map has the characteristic.

6. The cognitive impairment diagnostic apparatus according to claim 1,
wherein the video for diagnosis includes: a still image including an inducing image which induces visual hallucination; and a plurality of non-inducing images which do not induce visual hallucination,
the case characteristic data indicates that viewpoints are gathered in the inducing image, and
the diagnostic unit is configured to diagnose that there is a possibility of dementia with Lewy bodies included in cognitive impairment when the viewpoints are gathered in the inducing image in the distribution map.

7. The cognitive impairment diagnostic apparatus according to claim 1,
wherein the video for diagnosis includes a video of a moving object on the display surface,
the case characteristic data indicates that a viewpoint of the subject is unable to track the moving object, and
the diagnostic unit is configured to diagnose that there is a possibility of a decrease in cognitive function when the viewpoint has not tracked the moving object in the distribution map.

8. The cognitive impairment diagnostic apparatus according to claim 1,
wherein the diagnostic unit is further configured to calculate a viewpoint obtainment percentage indicating a percentage of viewpoints present on the display surface in the distribution map, and diagnose that there is a possibility of fronto-temporal dementia included in cognitive impairment when the viewpoint obtainment percentage is smaller than or equal to a predetermined value.

9. The cognitive impairment diagnostic apparatus according to claim 1,
wherein the video for diagnosis includes a first video, a second video, a third video, a fourth video, and a fifth video,
the first video includes an image of at least one of a person, an object, a landscape, or a graphic symbol,
the second video is a video including: a first image which includes a correct-answer graphic symbol and does not include any graphic symbol other than the correct-answer graphic symbol; and a second image which includes the correct-answer graphic symbol and a plurality of graphic symbols similar to the correct-answer graphic symbol,
the third video includes a still image of at least one of a person, an object, a landscape, or a graphic symbol,
the fourth video includes: a still image including an inducing graphic symbol which induces visual hallucination; and a plurality of non-inducing graphic symbols which do not induce visual hallucination, the fifth video includes a video of a moving object on the display surface, the display which displays each of the first video to the fifth video in a display period ranging from 10 seconds to 30 seconds inclusive, and the diagnostic unit is configured to diagnose whether there is a possibility of each of decreases in cognitive function, fronto-temporal dementia, corticobasal degeneration, and dementia with Lewy bodies, based on a distribution map corresponding to the display period of each of the first video to the fifth video.

10. The cognitive impairment diagnostic apparatus according to claim 9, wherein the diagnostic unit is further configured to calculate a viewpoint obtainment percentage indicating a percentage of viewpoints present on the display surface on the distribution map corresponding to each of the first video to the fifth video, invalidate a corresponding diagnostic result when the viewpoint obtainment percentage is smaller than or equal to a predetermined value, and diagnose that there is a possibility of fronto-temporal dementia included in cognitive impairment.

11. A non-transitory computer-readable recording medium storing a cognitive impairment diagnostic program recorded thereon, the cognitive impairment diagnostic program being for use in a computer which is connected to an imaging unit and a display including a display surface, and includes a storage unit which stores case characteristic data indicating characteristics of viewpoint distributions corresponding respectively to typical cases in cognitive impairment, the cognitive impairment diagnostic program causing the computer to execute:

displaying a video for diagnosis of cognitive impairment on a display surface;

capturing images of an eye of a subject, the capturing being performed by the imaging unit;

detecting viewpoints of the subject on the display surface in time series based on the images captured by the imaging unit;

creating a distribution map representing a distribution of the viewpoints detected; and diagnosing cognitive impairment of the subject by determining whether the distribution map has the characteristic indicated by the case characteristic data.

* * * * *